(12) United States Patent
Schmidt et al.

(10) Patent No.: US 6,849,438 B1
(45) Date of Patent: Feb. 1, 2005

(54) ISOLATED AND PURIFIED HUMAN SOLUBLE GUANYLYL CYCLASE α1/β1 (HSGCα1/β1)

(75) Inventors: Harald Schmidt, Giessen (DE); Ulrike Zabel, Rottendorf (DE); Wolfgang Poller, Berlin (DE)

(73) Assignee: Vasopharm Biotech GmbH, Wurzburg (DE)

( * ) Notice: Subject to any disclaimer, the term of this patent is extended or adjusted under 35 U.S.C. 154(b) by 0 days.

(21) Appl. No.: 09/762,767
(22) PCT Filed: Aug. 16, 1999
(86) PCT No.: PCT/DE99/02601

§ 371 (c)(1),
(2), (4) Date: Jun. 1, 2001

(87) PCT Pub. No.: WO00/09711

PCT Pub. Date: Feb. 24, 2000

(30) Foreign Application Priority Data

Aug. 14, 1998 (DE) .......................... 198 37 015

(51) Int. Cl.[7] ............................ C12N 9/00; C12N 9/16; C12N 1/20; C07H 21/04

(52) U.S. Cl. ............................... 435/196; 435/4; 435/6; 435/19; 435/183; 435/252.3; 435/320.1; 435/325; 530/350; 536/23.2; 536/23.3; 536/23.4; 536/23.5

(58) Field of Search .......................... 435/4, 6, 19, 69.1, 435/183–234, 196, 252.3, 320.1; 536/23.2, 23.4, 23.5; 530/350, 412, 413

(56) References Cited

PUBLICATIONS

Giuili et al. (FEBS Lett, vol. 304(1):83–88).*
Zabel et al. (Biochem J., vol. 335(1):51–57, 1998).*

* cited by examiner

Primary Examiner—Manjunath Rao
(74) Attorney, Agent, or Firm—Olson & Hierl, Ltd.

(57) ABSTRACT

The invention relates to the expression of the cDNA clone for sub-units a1 (hsGCa1) and b1 (hsGCb1) of human soluble guanylylcyclase and the subsequent purification of the active enzyme and use thereof, the medical application of the expression of this clone by gene transfer, in addition to antibodies against peptides derived from said sequence and the use thereof.

8 Claims, 23 Drawing Sheets a: nucleotide insertions
C95, C367, T891, G900, T903, G913, T1006, G1074, G1487, A1488, A1489, G2108, G2555, T2560 b: nucleotide delentions
T between G111 and T112, T between T2128 and G2129, T between G2975 and T2976 c: nucleotide exchanges
C1525>G, G2125>A

Figure 4
A
PCR determination of hsGCα1
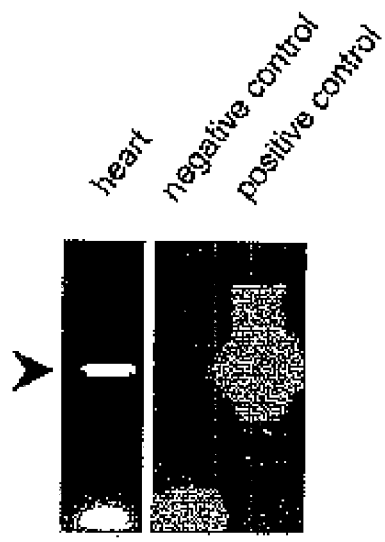
B
PCR determination of hsGCβ1
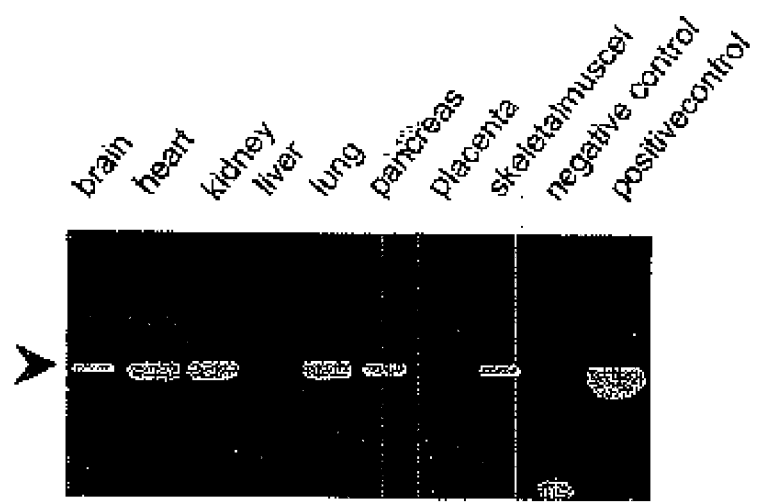

Figure 5
pVL1393 Baculovirus Transfer Vector
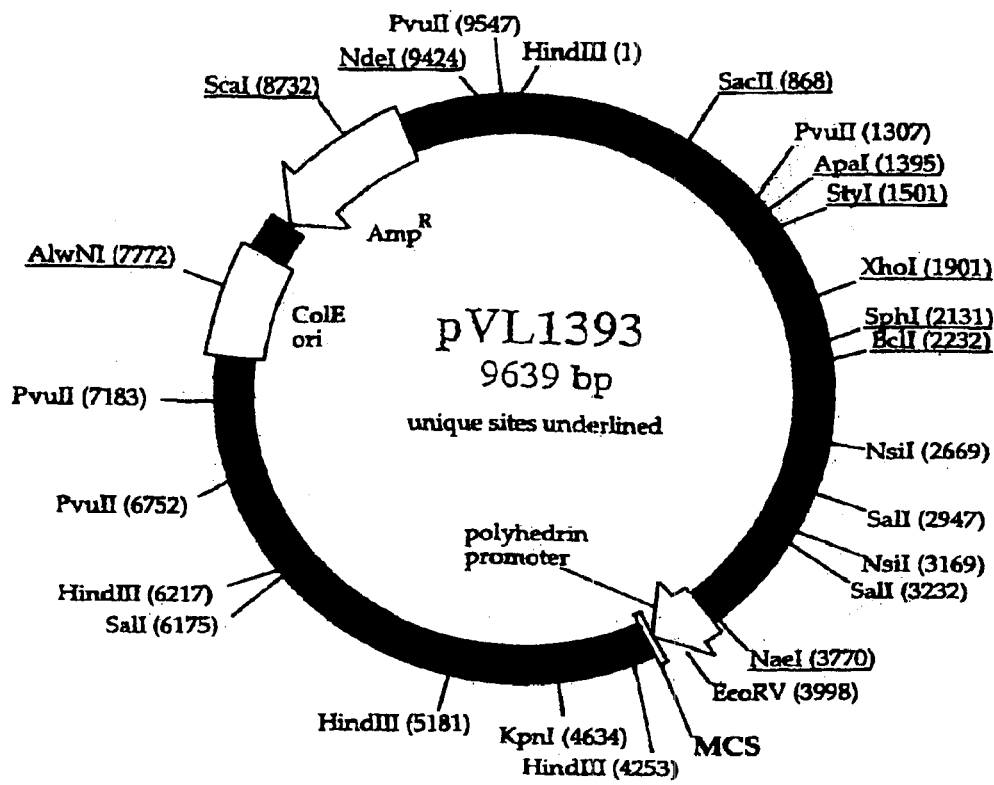
multiple cloning site (MCS) of pVL1393 with the unique restriction sites
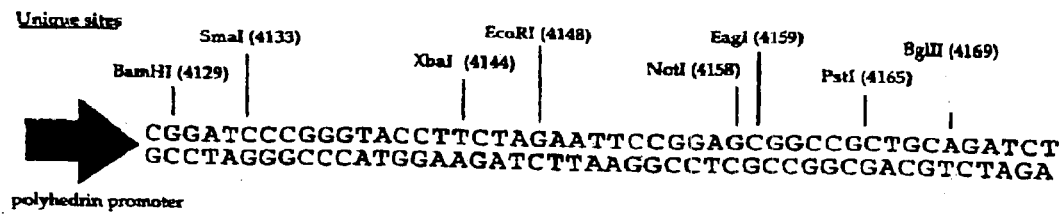

Figure 6
pAcG2T Baculovirus Transfer Vector
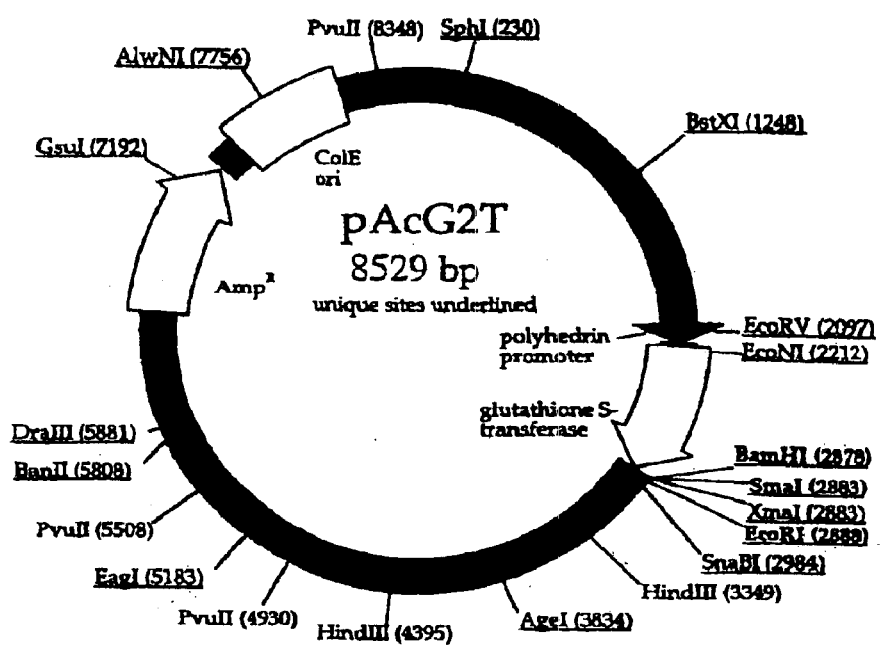
multiple cloning site (MCS) of pAcG2T downstream of glutathione-S-transferase sequence (GST) with the thrombin cleavage site and the unique restriction sites
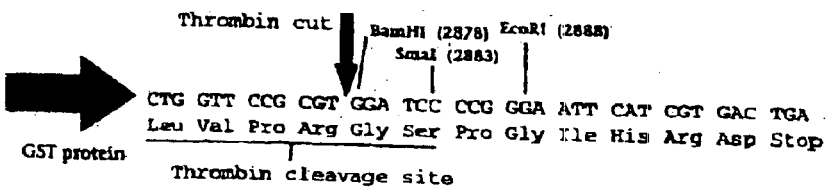

Figure 12: Purification of GST-hsGCalpha1/beta1 on GSH-Sepharose 4B

Figure 15: Purification of hsGC α1/β1 in a Coomassie stained SDS polyacryamide gel Figure 16: Construction of the hsGC-adenovectors Expression of human sGC in adenovirus-infected EA.hy926 cells

Figure 18

```
CCCTTATGGC GATTGGGCGG CTGCAGAGAC CAGGACTCAG TTCCCCTGCC CTAGTCTGAG
CCTAGTGGGT GGGACTCAGC TCAGAGTCAG TTTTCCAGAA GCAGGTTTCA GTGCAGAGTT
TTCCTACACT TTTCCTGCGC TAGAGCAGCG AGCAGCCTGG AACAGACCCA GGCGGAGGAC
ACCTGTGGGG GAGGGAGCGC CTGGAGGAGC TTAGAGACCC CAGCCGGGCG TGATCTCACC
ATGTGCGGAT TTGCGAGGCG CGCCCTGGAG CTGCTAGAGA TCCGGAAGCA CAGCCCCGAG
GTGTGCGAAG CCACCAAGAC TGCGGCTCTT GGAGAAAGCG TGAGCAGGGG GCCACCGCGG
TCTCCGCGCC TGTCTGCACC CTGTCGCCTG AGCTGCCTGA CAGTGACAAT GACATCCCAG
TTACCAGTGT CCTTGAATTG ATAGTGGCTT CTGTTTGTCA GTCTCATATA AGAACTACAG
CTCATCAGGA GGAGATCGCA GCAGGGTAAG AGACACCAAC ACCATGTTCT GCACGAAGCT
CAAGGATCTC AAGATCACAG GAGAGTGTCC TTTCTCCTTA CTGGCACCAG GTCAAGTTCC
TAACGAGTCT TCAGAGGAGG CAGCAGGAAG CTCAGAGAGC TGCAAAGCAA CCGTGCCCAT
CTGTCAAGAC ATTCCTGAGA AGAACATACA AGAAACTCTT CCTCAAAGAA AAACCAGTCG
GAGCCGAGTC TATCTTCACA CTTTGGCAGA GAGTATTTGC AAACTGATTT TCCCAGAGTT
TGAACGGCTG AATGTTGCAC TTCAGAGAAC ATTGGCAAAG CACAAAATAA AAGAAAGCAG
GAAATCTTTG GAAAGAGAAG ACTTTGAAAA AACAATTGCA GAGCAAGCAG TTGCAGCAGG
AGTTCCAGTG GAGGTTATCA AAGAATCTCT TGGTGAAGAG GTTTTTAAAA TATGTTACGA
GGAAGATGAA AACATCCTTG GGGTGGTTGG AGGCACCCTT AAAGATTTTT TAAACAGCTT
CAGTACCCTT CTGAAACAGA GCAGCCATTG CCAAGAAGCA GGAAAAAGGG GCAGGCTTGA
GGACGCCTCC ATTCTATGCC TGGATAAGGA GGATGATTTT CTACATGTTT ACTACTTCTT
CCCTAAGAGA ACCACCTCCC TGATTCTTCC CGGCATCATA AAGGCAGCTG CTCACGTATT
ATATGAAACG GAAGTGGAAG TGTCGTTAAT GCCTCCCTGC TTCCATAATG ATTGCAGCGA
GTTTGTGAAT CAGCCCTACT TGTTGTACTC CGTTCACATG AAAAGCACCA AGCCATCCCT
GTCCCCCAGC AAACCCCAGT CCTCGCTGGT GATTCCCACA TCGCTATTCT GCAAGACATT
TCCATTCCAT TTCATGTTTG ACAAAGATAT GACAATTCTG CAATTTGGCA ATGGCATCAG
AAGGCTGATG AACAGGAGAG ACTTTCAAGG AAAGCCTAAT TTTGAAGAAT ACTTTGAAAT
TCTGACTCCA AAAATCAACC AGACGTTTAG CGGGATCATG ACTATGTTGA ATATGCAGTT
TGTTGTACGA GTGAGGAGAT GGGACAACTC TGTCAAGAAA TCTTCAAGGG TTATGGACCT
CAAAGGCCAA ATGATCTACA TTGTTGAATC CAGTGCAATC TTGTTTTTGG GGTCACCCTG
TGTGGACAGA TTAGAAGATT TTACAGGACG AGGGCTCTAC CTCTCAGACA TCCCAATTCA
CAATGCACTG AGGGATGTGG TCTTAATAGG GGAACAAGCC CGAGCTCAAG ATGGCCTGAA
GAAGAGGCTG GGGAAGCTGA AGGCTACCCT TGAGCAAGCC CACCAAGCCC TGGAGGAGGA
GAAGAAAAAG ACAGTAGACC TTCTGTGCTC CATATTTCCC TGTGAGGTTG CTCAGCAGCT
GTGGCAAGGG CAAGTTGTGC AAGCCAAGAA GTTCAGTAAT GTCACCATGC TCTTCTCAGA
CATCGTTGGG TTCACTGCCA TCTGCTCCCA GTGCTCACCG CTGCAGGTCA TCACCATGCT
CAATGCACTG TACACTCGCT TCGACCAGCA GTGTGGAGAG CTGGATGTCT ACAAGGTGGA
GACCATTGGC GATGCCTATT GTGTAGCTGG GGGATTACAC AAAGAGAGTG ATACTCATGC
TGTTCAGATA GCGCTGATGG CCCTGAAGAT GATGGAGCTC TCTGATGAAG TTATGTCTCC
CCATGGAGAA CCTATCAAGA TGCGAATTGG ACTGCACTCT GGATCAGTTT TTGCTGGCGT
CGTTGGAGTT AAAATGCCCC GTTACTGTCT TTTTGGAAAC AATGTCACTC TGGCTAACAA
ATTTGAGTCC TGCAGTGTAC CACGAAAAAT CAATGTCAGC CCAACAACTT ACAGATTACT
CAAAGACTGT CCTGGTTTCG TGTTTACCCC TCGATCAAGG GAGGAACTTC CACCAAACTT
CCCTAGTGAA ATCCCCGGAA TCTGCCATTT TCTGGATGCT TACCAACAAG GAACAAACTC
AAAACCATGC TTCCAAAAGA AGATGTGGA AGATGGCAAT GCCAATTTTT TAGGCAAAGC
ATCAGGAATA GATTAGCAAC CTATATACCT ATTTATAAGT CTTTGGGGTT TGACTCATTG
AAGATGTGTA GAGCCTCTGA AAGCACTTTA GGGATTGTAG ATGGCTAACA AGCAGTATTA
AAATTTCAGG AGCCAAGTCA CAATCTTTCT CCTGTTTAAC ATGACAAAAT GTACTCACTT
CAGTACTTCA GCTCTTCAAG AAAAAAAAAA AAACCTTAAA AAGCTACTTT TGTGGGAGTA
TTTCTATTAT ATAACCAGCA CTTACTACCT GTACTCAAAA TTCAGCACCT TGTACATATA
TCAGATAATT GTAGTCAATT GTACAAACTG ATGGAGTCAC CTGCAATCTC ATATCCTGGT
GGAATGCCAT GGTTATTAAA GTGTGTTTGT GATAGTGTCG TCAAAAAAAA AAAAAAAAAA
                           AAAAAAAAAA AAAAA
```

Figure 19

```
Met Phe Cys Thr Lys Leu Lys Asp Leu Lys Ile Thr Gly Glu Cys Pro
Phe Ser Leu Leu Ala Pro Gly Gln Val Pro Asn Glu Ser Ser Glu Glu
Ala Ala Gly Ser Ser Glu Ser Cys Lys Ala Thr Val Pro Ile Cys Gln
Asp Ile Pro Glu Lys Asn Ile Gln Glu Ser Leu Pro Gln Arg Lys Thr
Ser Arg Ser Arg Val Tyr Leu His Thr Leu Ala Glu Ser Ile Cys Lys
Leu Ile Phe Pro Glu Phe Glu Arg Leu Asn Val Ala Leu Gln Arg Thr
Leu Ala Lys His Lys Ile Lys Glu Ser Arg Lys Ser Leu Glu Arg Glu
Asp Phe Glu Lys Thr Ile Ala Glu Gln Ala Val Ala Ala Gly Val Pro
Val Glu Val Ile Lys Glu Ser Leu Gly Glu Glu Val Phe Lys Ile Cys
Tyr Glu Glu Asp Glu Asn Ile Leu Gly Val Val Gly Gly Thr Leu Lys
Asp Phe Leu Asn Ser Phe Ser Thr Leu Leu Lys Gln Ser Ser His Cys
Gln Glu Ala Gly Lys Arg Gly Arg Leu Glu Asp Ala Ser Ile Leu Cys
Leu Asp Lys Glu Asp Asp Phe Leu His Val Tyr Tyr Phe Phe Pro Lys
Arg Thr Thr Ser Leu Ile Leu Pro Gly Ile Ile Lys Ala Ala Ala His
Val Leu Tyr Glu Thr Glu Val Glu Val Ser Leu Met Pro Pro Cys Phe
His Asn Asp Cys Ser Glu Phe Val Asn Gln Pro Tyr Leu Leu Tyr Ser
Val His Met Lys Ser Thr Lys Pro Ser Leu Ser Pro Ser Lys Pro Gln
Ser Ser Leu Val Ile Pro Thr Ser Leu Phe Cys Lys Thr Phe Pro Phe
His Phe Met Phe Asp Lys Asp Met Thr Ile Leu Gln Phe Gly Asn Gly
Ile Arg Arg Leu Met Asn Arg Arg Asp Phe Gln Gly Lys Pro Asn Phe
Glu Glu Tyr Phe Glu Ile Leu Thr Pro Lys Ile Asn Gln Thr Phe Ser
Gly Ile Met Thr Met Leu Asn Met Gln Phe Val Val Arg Val Arg Arg
Trp Asp Asn Ser Val Lys Lys Ser Ser Arg Val Met Asp Leu Lys Gly
Gln Met Ile Tyr Ile Val Glu Ser Ser Ala Ile Leu Phe Leu Gly Ser
Pro Cys Val Asp Arg Leu Glu Asp Phe Thr Gly Arg Gly Leu Tyr Leu
Ser Asp Ile Pro Ile His Asn Ala Leu Arg Asp Val Val Leu Ile Gly
Glu Gln Ala Arg Ala Gln Asp Gly Leu Lys Lys Arg Leu Gly Lys Leu
Lys Ala Thr Leu Glu Gln Ala His Gln Ala Leu Glu Glu Glu Lys Lys
Lys Thr Val Asp Leu Leu Cys Ser Ile Phe Pro Cys Glu Val Ala Gln
Gln Leu Trp Gln Gly Gln Val Val Gln Ala Lys Lys Phe Ser Asn Val
Thr Met Leu Phe Ser Asp Ile Val Gly Phe Thr Ala Ile Cys Ser Gln
Cys Ser Pro Leu Gln Val Ile Thr Met Leu Asn Ala Leu Tyr Thr Arg
Phe Asp Gln Gln Cys Gly Glu Leu Asp Val Tyr Lys Val Glu Thr Ile
Gly Asp Ala Tyr Cys Val Ala Gly Gly Leu His Lys Glu Ser Asp Thr
His Ala Val Gln Ile Ala Leu Met Ala Leu Lys Met Met Glu Leu Ser
Asp Glu Val Met Ser Pro His Gly Glu Pro Ile Lys Met Arg Ile Gly
Leu His Ser Gly Ser Val Phe Ala Gly Val Val Gly Val Lys Met Pro
Arg Tyr Cys Leu Phe Gly Asn Asn Val Thr Leu Ala Asn Lys Phe Glu
Ser Cys Ser Val Pro Arg Lys Ile Asn Val Ser Pro Thr Thr Tyr Arg
Leu Leu Lys Asp Cys Pro Gly Phe Val Phe Thr Pro Arg Ser Arg Glu
Glu Leu Pro Pro Asn Phe Pro Ser Glu Ile Pro Gly Ile Cys His Phe
Leu Asp Ala Tyr Gln Gln Gly Thr Asn Ser Lys Pro Cys Phe Gln Lys
Lys Asp Val Glu Asp Gly Asn Ala Asn Phe Leu Gly Lys Ala Ser Gly
Ile Asp End
```

Figure 20

```
CCCCCCCCCG CCGCTGCCGC CTCTGCCTGG GTCCCTTCGG CCGTACCTCT GCGTGGGGGC
TGCCTCCCCG GCTCCCGGTG CAGACACCAT GTACGGATTT GTGAATCACG CCCTGGAGTT
GCTGGTGATC CGCAATTACG GCCCCGAGGT GTGGGAAGAC ATCAAAAAAG AGGCACAGTT
AGATGAAGAA GGACAGTTTC TTGTCAGAAT AATATATGAT CACTCCAAAA CTTATGATTT
GGTTGCTGCT GCAAGCAAAG TCCTCAATCT CAATGCTGCA GAAATCCTCC AAATGTTTGG
GAAGATGTTT TTCGTCTTTT GCCAAGAATC TGGTTATGAT ACAATCTTGC GTGTCCTGGG
CTCTAATGTC AGAGAATTTC TACAGAACCT TGATGCTCTG CACGACCACC TTGCTACCAT
CTACCCAGGA ATGCGTGCAC CTTCCTTTAG GTGCACTGAT GCAGAAAAGG GCAAAGGACT
CATTTTGCAC TACTACTCAG AGAGAGAAGG ACTTCAGGAT ATTGTCATTG GAATCATCAA
AACAGTGGCA CAACAAATCC ATGGCACTGA AATAGACATG AAGGTTATTC AGCAAAGAAA
TGAAGAATGT GATCATACTC AATTTTTAAT TGAAGAAAAA GAGTCAAAAG AAGAGGATTT
TTATGAAGAT CTTGACAGAT TTGAAGAAAA TGGTACCCAG GAATCACGCA TCAGCCCATA
TACATTCTGC AAAGCTTTTC CTTTTCATAT AATATTTGAC CGGGACCTAG TGGTCACTCA
GTGTGGCAAT GCTATATACA GAGTTCTCCC CCAGCTCCAG CCTGGGAATT CCAGCCTTCT
GTCTGTCTTC TCGCTGGTTC GTCCTCATAT TGATATTAGT TTCCATGGGA TCCTTTCTCA
CATCAATACT GTTTTTGTAT TGAGAAGCAA GGAAGGATTG TTGGATGTGG AGAAATTAGA
ATGTGAGGAT GAACTGACTG GGACTGAGAT CAGCTGCTTA CGTCTCAAGG GTCAAATGAT
CTACTTACCT GAAGCAGATA GCATACTTTT TCTATGTTCA CCAAGTGTCA TGAACCTGGA
CGATTTGACA AGGAGAGGGC TGTATCTAAG TGACATCCCT CTGCATGATG CCACGCGCGA
TCTTGTTCTT TTGGGAGAAC AATTTAGAGA GGAATACAAA CTCACCCAAG AACTGGAAAT
CCTCACTGAC AGGCTACAGC TCACGTTAAG AGCCCTGGAA GATGAAAACA AAAACACAGA
CACATTGCTG TATTCTGTCC TTCCTCCGTC TGTTGCCAAT GAGCTGCGGC ACAAGCGTCC
AGTGCCTGCC AAAAGATATG ACAATGTGAC CATCCTCTTT AGTGGCATTG TGGGCTTCAA
TGCTTTCTGT AGCAAGCATG CATCTGGAGA AGGAGCCATG AAGATCGTCA ACCTCCTCAA
CGACCTCTAC ACCAGATTTG ACACACTGAC TGATTCCCGG AAAAACCCAT TTGTTTATAA
GGTGGAGACT GTTGGTGACA AGTATATGAC AGTGAGTGGT TTACCAGAGC CATGCATTCA
CCATGCACGA TCCATCTGCC ACCTGGCCTT GCACATGATG GAAATTGCTG GCCAGGTTCA
AGTAGATGGT GAATCTGTTC AGATAACAAT AGGGATACAC ACTGGAGAGG TAGTTACAGG
TGTCATAGGA CAGCGGATGC CTCGATACTG TCTTTTTGGG AATACTGTCA ACCTCACAAG
CCGAACAGAA ACCACAGGAG AAAAGGGAAA AATAAATGTG TCTGAATATA CATACAGATG
TCTTATGTCT CCAGAAAATT CAGATCCACA ATTCCACTTG GAGCACAGAG GCCCAGTGTC
CATGAAGGGC AAAAAAGAAC CAATGCAAGT TTGGTTTCTA TCCAGAAAAA ATACAGGAAC
AGAGGAAACA AAGCAGGATG ATGACTGAAT CTTGGATTAT GGGGTGAAGA GGAGTACAGA
CTAGGTTCCA GTTTTCTCCT AACACGTGCC AAGCCCAGGA GCAGTTCTTC CCTATGGATA
CAGATTTTCT TTTGTCCTTG TCCATTACCC CAAGACTTTC TTCTAGATAT ATCTCTCACT
ATCCGTTATT CAACCTTAGC TCTGCTTTCT ATTACTTTTT AGGCTTTAGT ATATTATCTA
AAGTTTGGCT TTTGATGTGG ATGATGTGAG CTTCATGTGT CTTAAAATCT ACTACAAGCA
TTACCTAACA TGGTGATCTG CAAGTAGTAG GCACCCAATA AATATTTGTT GAATTTAGTT
AAATGAAACT GAACAGTGTT TGGCCATGTG TATATTTATA TCATGTTTAC CAAATCTGTT
TAGTGTTCCA CATATATGTA TATGTATATT TTAATGACTA TAATGTAATA AAGTTTATAT
           CATGTTGGTG TATATCATTA TAGAAATCAT TTTCTAAAGG AGT
```

Figure 21

```
Met Tyr Gly Phe Val Asn His Ala Leu Glu Leu Leu Val Ile Arg Asn
Tyr Gly Pro Glu Val Trp Glu Asp Ile Lys Lys Glu Ala Gln Leu Asp
Glu Glu Gly Gln Phe Leu Val Arg Ile Ile Tyr Asp Asp Ser Lys Thr
Tyr Asp Leu Val Ala Ala Ala Ser Lys Val Leu Asn Leu Asn Ala Gly
Glu Ile Leu Gln Met Phe Gly Lys Met Phe Phe Val Phe Cys Gln Glu
Ser Gly Tyr Asp Thr Ile Leu Arg Val Leu Gly Ser Asn Val Arg Glu
Phe Leu Gln Asn Leu Asp Ala Leu His Asp His Leu Ala Thr Ile Tyr
Pro Gly Met Arg Ala Pro Ser Phe Arg Cys Thr Asp Ala Glu Lys Gly
Lys Gly Leu Ile Leu His Tyr Tyr Ser Glu Arg Glu Gly Leu Gln Asp
Ile Val Ile Gly Ile Ile Lys Thr Val Ala Gln Gln Ile His Gly Thr
Glu Ile Asp Met Lys Val Ile Gln Gln Arg Asn Glu Glu Cys Asp His
Thr Gln Phe Leu Ile Glu Glu Lys Glu Ser Lys Glu Glu Asp Phe Tyr
Glu Asp Leu Asp Arg Phe Glu Glu Asn Gly Thr Gln Glu Ser Arg Ile
Ser Pro Tyr Thr Phe Cys Lys Ala Phe Pro Phe His Ile Ile Phe Asp
Arg Asp Leu Val Val Thr Gln Cys Gly Asn Ala Ile Tyr Arg Val Leu
Pro Gln Leu Gln Pro Gly Asn Cys Ser Leu Leu Ser Val Phe Ser Leu
Val Arg Pro His Ile Asp Ile Ser Phe His Gly Ile Leu Ser His Ile
Asn Thr Val Phe Val Leu Arg Ser Lys Glu Gly Leu Leu Asp Val Glu
Lys Leu Glu Cys Glu Asp Glu Leu Thr Gly Thr Glu Ile Ser Cys Leu
Arg Leu Lys Gly Gln Met Ile Tyr Leu Pro Glu Ala Asp Ser Ile Leu
Phe Leu Cys Ser Pro Ser Val Met Asn Leu Asp Asp Leu Thr Arg Arg
Gly Leu Tyr Leu Ser Asp Ile Pro Leu His Asp Ala Thr Arg Asp Leu
Val Leu Leu Gly Glu Gln Phe Arg Glu Glu Tyr Lys Leu Thr Gln Glu
Leu Glu Ile Leu Thr Asp Arg Leu Gln Leu Thr Leu Arg Ala Leu Glu
Asp Glu Lys Lys Lys Thr Asp Thr Leu Leu Tyr Ser Val Leu Pro Pro
Ser Val Ala Asn Glu Leu Arg His Lys Arg Pro Val Pro Ala Lys Arg
Tyr Asp Asn Val Thr Ile Leu Phe Ser Gly Ile Val Gly Phe Asn Ala
Phe Cys Ser Lys His Ala Ser Gly Glu Gly Ala Met Lys Ile Val Asn
Leu Leu Asn Asp Leu Tyr Thr Arg Phe Asp Thr Leu Thr Asp Ser Arg
Lys Asn Pro Phe Val Tyr Lys Val Glu Thr Val Gly Asp Lys Tyr Met
Thr Val Ser Gly Leu Pro Glu Pro Cys Ile His His Ala Arg Ser Ile
Cys His Leu Ala Leu Asp Met Met Glu Ile Ala Gly Gln Val Gln Val
Asp Gly Glu Ser Val Gln Ile Thr Ile Gly Ile His Thr Gly Glu Val
Val Thr Gly Val Ile Gly Gln Arg Met Pro Arg Tyr Cys Leu Phe Gly
Asn Thr Val Asn Leu Thr Ser Arg Thr Glu Thr Thr Gly Glu Lys Gly
Lys Ile Asn Val Ser Glu Tyr Thr Tyr Arg Cys Leu Met Ser Pro Glu
Asn Ser Asp Pro Gln Phe His Leu Glu His Arg Gly Pro Val Ser Met
Lys Gly Lys Lys Glu Pro Met Gln Val Trp Phe Leu Ser Arg Lys Asn
Thr Gly Thr Glu Glu Thr Lys Gln Asp Asp Asp end
```

Figure 22

Phe Thr Pro Arg Ser Arg Glu Glu Leu Pro Pro Asn Phe Pro

Figure 23

Lys Gly Lys Lys Glu Pro Met Gln Val Trp Phe Leu Ser Arg Lys Asn
Thr Gly Thr Glu Glu Thr

Figure 24 upper primer

AAAAGGATCC ATGTTCTGCA CGAAGCTC lower primer

ATTATGGAAG CAGGGAGG

Figure 25 upper primer

AAAAGGATCC ATGTACGGAT TTGTGAAT lower primer

ATGCGTGATT CCTGGGTACC

```
                          SEQUENCE LISTING

<160> NUMBER OF SEQ ID NOS: 19

<210> SEQ ID NO 1
<211> LENGTH: 3015
<212> TYPE: DNA
<213> ORGANISM: homo sapiens

<400> SEQUENCE: 1
cccttatggc gattgggcgg ctgcagagac caggactcag ttcccctgcc ctagtctgag      60
cctagtgggt gggactcagc tcagagtcag ttttccagaa gcaggtttca gtgcagagtt     120
ttcctacact tttcctgcgc tagagcagcg agcagcctgg aacagaccca ggcggaggac     180
acctgtgggg gagggagcgc ctggaggagc ttagagaccc cagccgggcg tgatctcacc     240
```

-continued

```
atgtgcggat tgcgaggcg cgccctggag ctgctagaga tccggaagca cagccccgag     300
gtgtgcgaag ccaccaagac tgcggctctt ggagaaagcg tgagcagggg gccaccgcgg     360
tctccgcgcc tgtctgcacc ctgtcgcctg agctgcctga cagtgacaat gacatcccag     420
ttaccagtgt ccttgaattg atagtggctt ctgtttgtca gtctcatata agaactacag     480
ctcatcagga ggagatcgca gcagggtaag agacaccaac accatgttct gcacgaagct     540
caaggatctc aagatcacag gagagtgtcc tttctcctta ctggcaccag gtcaagttcc     600
taacgagtct tcagaggagg cagcaggaag ctcagagagc tgcaaagcaa ccgtgcccat     660
ctgtcaagac attcctgaga gaacataca  agaaagtctt cctcaaagaa aaccagtcg      720
gagccgagtc tatcttcaca ctttggcaga gagtatttgc aaactgattt tcccagagtt     780
tgaacggctg aatgttgcac ttcagagaac attggcaaag cacaaaataa agaaagcag     840
gaaatctttg gaaagagaag actttgaaaa acaattgca gagcaagcag ttgcagcagg     900
agttccagtg gaggttatca agaatctct tggtgaagag gtttttaaaa tatgttacga      960
ggaagatgaa acatccttg gggtggttgg aggcacccctt aaagattttt taaacagctt   1020
cagtacccctt ctgaaacaga gcagccattg ccaagaagca ggaaaaaggg gcaggcttga   1080
ggacgcctcc attctatgcc tggataagga ggatgattt ctacatgttt actacttctt    1140
ccctaagaga accacctccc tgattcttcc cggcatcata aggcagctg ctcacgtatt     1200
atatgaaacg gaagtggaag tgtcgttaat gcctccctgc ttccataatg attgcagcga   1260
gtttgtgaat cagccctact tgttgtactc cgttcacatg aaaagcacca agccatccct   1320
gtcccccagc aaaccccagt cctcgctggt gattcccaca tcgctattct gcaagacatt   1380
tccattccat ttcatgtttg acaaagatat gacaattctg caatttggca atggcatcag   1440
aaggctgatg aacaggagag actttcaagg aaagcctaat tttgaagaat actttgaaat   1500
tctgactcca aaaatcaacc agacgtttag cgggatcatg actatgttga atatgcagtt   1560
tgttgtacga gtgaggagat gggacaactc tgtgaagaaa tcttcaaggg ttatggacct   1620
caaaggccaa atgatctaca ttgttgaatc cagtgcaatc ttgtttttgg ggtcaccctg   1680
tgtggacaga ttagaagatt ttacaggacg agggctctac ctctcagaca tcccaattca   1740
caatgcactg agggatgtgg tcttaatagg gaacaagcc  cgagctcaag atggcctgaa   1800
gaagaggctg gggaagctga aggctaccct tgagcaagcc caccaagccc tggaggagga   1860
gaagaaaaag acagtagacc ttctgtgctc catatttccc tgtgaggttg ctcagcagct   1920
gtggcaaggg caagttgtgc aagccaagaa gttcagtaat gtcaccatgc tcttctcaga   1980
catcgttggg ttcactgcca tctgctccca gtgctcaccg ctgcaggtca tcaccatgct   2040
caatgcactg tacactcgct tcgaccagca gtgtggagag ctggatgtct acaaggtgga   2100
gaccattggc gatgcctatt gtgtagctgg gggattacac aaagagagtg atactcatgc   2160
tgttcagata gcgctgatgg cccctgaagat gatggagctc tctgatgaag ttatgtctcc   2220
ccatggagaa cctatcaaga tgcgaattgg actgcactct ggatcagttt ttgctggcgt   2280
cgttggagtt aaaatgcccc gttactgtct ttttggaaac aatgtcactc tggctaacaa   2340
atttgagtcc tgcagtgtac cacgaaaaat caatgtcagc ccaacaactt acagattact   2400
caaagactgt cctggtttcg tgtttacccc tcgatcaagg gaggaacttc caccaaactt   2460
ccctagtgaa atccccggaa tctgccattt tctggatgct taccaacaag gaacaaactc   2520
aaaaccatgc ttccaaaaga aagatgtgga agatggcaat gccaatttttt taggcaaagc   2580
```

|   |   |   |   |   |   |   |   |   |   |
|---|---|---|---|---|---|---|---|---|---|
| atcaggaata | gattagcaac | ctatatacct | atttataagt | ctttggggtt | tgactcattg | 2640 |
| aagatgtgta | gagcctctga | aagcacttta | gggattgtag | atggctaaca | agcagtatta | 2700 |
| aaatttcagg | agccaagtca | caatctttct | cctgtttaac | atgacaaaat | gtactcactt | 2760 |
| cagtacttca | gctcttcaag | aaaaaaaaaa | aaaccttaaa | aagctacttt | tgtgggagta | 2820 |
| tttctattat | ataaccagca | cttactacct | gtactcaaaa | ttcagcacct | tgtacatata | 2880 |
| tcagataatt | gtagtcaatt | gtacaaactg | atggagtcac | ctgcaatctc | atatcctggt | 2940 |
| ggaatgccat | ggttattaaa | gtgtgtttgt | gatagtgtcg | tcaaaaaaaa | aaaaaaaaa | 3000 |
| aaaaaaaaaa | aaaaa |   |   |   |   | 3015 |

<210> SEQ ID NO 2
<211> LENGTH: 688
<212> TYPE: PRT
<213> ORGANISM: homo sapiens

<400> SEQUENCE: 2

Met Phe Cys Thr Lys Leu Lys Asp Leu Lys Ile Thr Gly Glu Cys Pro
1               5                   10                  15

Phe Ser Leu Leu Ala Pro Gly Gln Val Pro Asn Glu Ser Ser Glu Glu
            20                  25                  30

Ala Ala Gly Ser Ser Glu Ser Cys Lys Ala Thr Val Pro Ile Cys Gln
        35                  40                  45

Asp Ile Pro Glu Lys Asn Ile Gln Glu Ser Leu Pro Gln Arg Lys Thr
    50                  55                  60

Ser Arg Ser Arg Val Tyr Leu His Thr Leu Ala Glu Ser Ile Cys Lys
65                  70                  75                  80

Leu Ile Phe Pro Glu Phe Glu Arg Leu Asn Val Ala Leu Gln Arg Thr
                85                  90                  95

Leu Ala Lys His Lys Ile Lys Glu Ser Arg Lys Ser Leu Glu Arg Glu
            100                 105                 110

Asp Phe Glu Lys Thr Ile Ala Glu Gln Ala Val Ala Ala Gly Val Pro
        115                 120                 125

Val Glu Val Ile Lys Glu Ser Leu Gly Glu Val Phe Lys Ile Cys
130                 135                 140

Tyr Glu Glu Asp Glu Asn Ile Leu Gly Val Val Gly Gly Thr Leu Lys
145                 150                 155                 160

Asp Phe Leu Asn Ser Phe Ser Thr Leu Leu Lys Gln Ser Ser His Cys
                165                 170                 175

Gln Glu Ala Gly Lys Arg Gly Arg Leu Glu Asp Ala Ser Ile Leu Cys
            180                 185                 190

Leu Asp Lys Glu Asp Phe Leu His Val Tyr Tyr Phe Phe Pro Lys
        195                 200                 205

Arg Thr Thr Ser Leu Ile Leu Pro Gly Ile Ile Lys Ala Ala Ala His
    210                 215                 220

Val Leu Tyr Glu Thr Glu Val Glu Val Ser Leu Met Pro Pro Cys Phe
225                 230                 235                 240

His Asn Asp Cys Ser Glu Phe Val Asn Gln Pro Tyr Leu Leu Tyr Ser
                245                 250                 255

Val His Met Lys Ser Thr Lys Pro Ser Leu Ser Pro Ser Lys Pro Gln
            260                 265                 270

Ser Ser Leu Val Ile Pro Thr Ser Leu Phe Cys Lys Thr Phe Pro Phe
        275                 280                 285

His Phe Met Phe Asp Lys Asp Met Thr Ile Leu Gln Phe Gly Asn Gly

-continued

```
              290                 295                 300
Ile Arg Arg Leu Met Asn Arg Arg Asp Phe Gln Gly Lys Pro Asn Phe
305                 310                 315                 320

Glu Glu Tyr Phe Glu Ile Leu Thr Pro Lys Ile Asn Gln Thr Phe Ser
                325                 330                 335

Gly Ile Met Thr Met Leu Asn Met Gln Phe Val Val Arg Val Arg Arg
                340                 345                 350

Trp Asp Asn Ser Val Lys Lys Ser Arg Val Met Asp Leu Lys Gly
                355                 360             365

Gln Met Ile Tyr Ile Val Glu Ser Ser Ala Ile Leu Phe Leu Gly Ser
370                 375                 380

Pro Cys Val Asp Arg Leu Glu Asp Phe Thr Gly Arg Gly Leu Tyr Leu
385                 390                 395                 400

Ser Asp Ile Pro Ile His Asn Ala Leu Arg Asp Val Val Leu Ile Gly
                405                 410                 415

Glu Gln Ala Arg Ala Gln Asp Gly Leu Lys Lys Arg Leu Gly Lys Leu
                420                 425                 430

Lys Ala Thr Leu Glu Gln Ala His Gln Ala Leu Glu Glu Lys Lys
                435                 440                 445

Lys Thr Val Asp Leu Leu Cys Ser Ile Phe Pro Cys Glu Val Ala Gln
                450                 455                 460

Gln Leu Trp Gln Gly Gln Val Val Gln Ala Lys Lys Phe Ser Asn Val
465                 470                 475                 480

Thr Met Leu Phe Ser Asp Ile Val Gly Phe Thr Ala Ile Cys Ser Gln
                485                 490                 495

Cys Ser Pro Leu Gln Val Ile Thr Met Leu Asn Ala Leu Tyr Thr Arg
                500                 505                 510

Phe Asp Gln Gln Cys Gly Glu Leu Asp Val Tyr Lys Val Glu Thr Ile
                515                 520                 525

Gly Asp Ala Tyr Cys Val Ala Gly Gly Leu His Lys Glu Ser Asp Thr
                530                 535                 540

His Ala Val Gln Ile Ala Leu Met Ala Leu Lys Met Met Glu Leu Ser
545                 550                 555                 560

Asp Glu Val Met Ser Pro His Gly Glu Pro Ile Lys Met Arg Ile Gly
                565                 570                 575

Leu His Ser Gly Ser Val Phe Ala Gly Val Val Gly Val Lys Met Pro
                580                 585                 590

Arg Tyr Cys Leu Phe Gly Asn Asn Val Thr Leu Ala Asn Lys Phe Glu
                595                 600                 605

Ser Cys Ser Val Pro Arg Lys Ile Asn Val Ser Pro Thr Thr Tyr Arg
610                 615                 620

Leu Leu Lys Asp Cys Pro Gly Phe Val Phe Thr Pro Arg Ser Arg Glu
625                 630                 635                 640

Glu Leu Pro Pro Asn Phe Pro Ser Glu Ile Pro Gly Ile Cys His Phe
                645                 650                 655

Leu Asp Ala Tyr Gln Gln Gly Thr Asn Ser Lys Pro Cys Phe Gln Lys
                660                 665                 670

Lys Asp Val Glu Asp Gly Asn Ala Asn Phe Leu Gly Lys Ala Ser Gly
                675                 680                 685
```

<210> SEQ ID NO 3
<211> LENGTH: 2443
<212> TYPE: DNA
<213> ORGANISM: homo sapiens

<400> SEQUENCE: 3

```
cccccccccg ccgctgccgc ctctgcctgg gtcccttcgg ccgtacctct gcgtgggggc      60
tgcctccccg gctcccggtg cagacaccat gtacggattt gtgaatcacg ccctggagtt     120
gctggtgatc cgcaattacg gccccgaggt gtgggaagac atcaaaaaag aggcacagtt     180
agatgaagaa ggacagtttc ttgtcagaat aatatatgat gactccaaaa cttatgattt     240
ggttgctgct gcaagcaaag tcctcaatct caatgctgga gaaatcctcc aaatgtttgg     300
gaagatgttt ttcgtctttt gccaagaatc tggttatgac aatcttgc gtgtcctggg       360
ctctaatgtc agagaatttc tacagaacct tgatgctctg cacgaccacc ttgctaccat     420
ctacccagga atgcgtgcac cttcctttag gtgcactgat gcagaaaagg caaaggact     480
cattttgcac tactactcag agagagaagg acttcaggat attgtcattg aatcatcaa     540
aacagtggca caacaaatcc atggcactga atagacatg aaggttattc agcaaagaaa      600
tgaagaatgt gatcatactc aattttttaat tgaagaaaaa gagtcaaaag aagaggattt    660
ttatgaagat cttgacagat tgaagaaaa tggtacccag gaatcacgca tcagcccata     720
tacattctgc aaagcttttc cttttcatat aatatttgac cgggacctag tggtcactca     780
gtgtggcaat gctatataca gagttctccc ccagctccag cctgggaatt gcagccttct     840
gtctgtcttc tcgctggttc gtcctcatat tgatattagt ttccatggga tcctttctca    900
catcaatact gttttttgtat tgagaagcaa ggaaggattg ttggatgtgg agaaattaga    960
atgtgaggat gaactgactg ggactgagat cagctgctta cgtctcaagg gtcaaatgat   1020
ctacttacct gaagcagata gcatacttt tctatgttca ccaagtgtca tgaacctgga    1080
cgatttgaca aggagagggc tgtatctaag tgacatccct ctgcatgatg ccacgcgcga   1140
tcttgttctt tgggagaac aatttagaga ggaatacaaa ctcacccaag aactggaaat   1200
cctcactgac aggctacagc tcacgttaag agccctggaa gatgaaaaga aaagacaga    1260
cacattgctg tattctgtcc ttcctccgtc tgttgccaat gagctgcggc acaagcgtcc   1320
agtgcctgcc aaaagatatg acaatgtgac catcctcttt agtggcattg tgggcttcaa   1380
tgctttctgt agcaagcatg catctggaga aggagccatg aagatcgtca acctcctcaa   1440
cgacctctac accagatttg acacactgac tgattcccgg aaaaacccat ttgtttataa   1500
ggtggagact gttggtgaca gtatatgac agtgagtggt ttaccagagc catgcattca   1560
ccatgcacga tccatctgcc acctggcctt ggacatgatg gaaattgctg gccaggttca   1620
agtagatggt gaatctgttc agataacaat agggatacac actggagagg tagttacagg   1680
tgtcatagga cagcggatgc ctcgatactg tctttttggg aatactgtca acctcacaag   1740
ccgaacagaa accacaggag aaaagggaaa ataaatgtg tctgaatata catacagatg   1800
tcttatgtct ccagaaaatt cagatccaca attccacttg gagcacagag gcccagtgtc   1860
catgaagggc aaaaaagaac caatgcaagt ttggtttcta tccagaaaaa atacaggaac   1920
agaggaaaca aagcaggatg atgactgaat cttggattat ggggtgaaga ggagtacaga   1980
ctaggttcca gttttctcct aacacgtgcc aagcccagga gcagttcttc cctatggata   2040
cagattttct tttgtccttg tccattaccc caagactttc ttctagatat atctctcact   2100
atccgttatt caaccttagc tctgctttct attactttt aggctttagt atattatcta   2160
aagtttggct tttgatgtgg atgatgtgag cttcatgtgt cttaaaatct actacaagca   2220
ttacctaaca tggtgatctg caagtagtag gcacccaata aatatttgtt gaatttagtt   2280
```

-continued

```
aaatgaaact gaacagtgtt tggccatgtg tatatttata tcatgtttac caaatctgtt    2340
tagtgttcca catatatgta tatgtatatt ttaatgacta taatgtaata aagtttatat    2400
catgttggtg tatatcatta tagaaatcat tttctaaagg agt                       2443
```

<210> SEQ ID NO 4
<211> LENGTH: 619
<212> TYPE: PRT
<213> ORGANISM: homo sapiens

<400> SEQUENCE: 4

```
Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ser Lys Val Leu Asn Leu Asn Ala Gly
    50                  55                  60

Glu Ile Leu Gln Met Phe Gly Lys Met Phe Val Phe Cys Gln Glu
 65              70                  75                  80

Ser Gly Tyr Asp Thr Ile Leu Arg Val Leu Gly Ser Asn Val Arg Glu
            85                  90                  95

Phe Leu Gln Asn Leu Asp Ala Leu His Asp Leu Ala Thr Ile Tyr
        100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350
```

```
Val Leu Leu Gly Glu Gln Phe Arg Glu Tyr Lys Leu Thr Gln Glu
            355                 360                 365

Leu Glu Ile Leu Thr Asp Arg Leu Gln Leu Thr Leu Arg Ala Leu Glu
    370                 375                 380

Asp Glu Lys Lys Lys Thr Asp Thr Leu Leu Tyr Ser Val Leu Pro Pro
385                 390                 395                 400

Ser Val Ala Asn Glu Leu Arg His Lys Arg Pro Val Pro Ala Lys Arg
                405                 410                 415

Tyr Asp Asn Val Thr Ile Leu Phe Ser Gly Ile Val Gly Phe Asn Ala
                420                 425                 430

Phe Cys Ser Lys His Ala Ser Gly Glu Gly Ala Met Lys Ile Val Asn
                435                 440                 445

Leu Leu Asn Asp Leu Tyr Thr Arg Phe Asp Thr Leu Thr Asp Ser Arg
            450                 455                 460

Lys Asn Pro Phe Val Tyr Lys Val Glu Thr Val Gly Asp Lys Tyr Met
465                 470                 475                 480

Thr Val Ser Gly Leu Pro Glu Pro Cys Ile His His Ala Arg Ser Ile
                485                 490                 495

Cys His Leu Ala Leu Asp Met Met Glu Ile Ala Gly Gln Val Gln Val
            500                 505                 510

Asp Gly Glu Ser Val Gln Ile Thr Ile Gly Ile His Thr Gly Glu Val
            515                 520                 525

Val Thr Gly Val Ile Gly Gln Arg Met Pro Arg Tyr Cys Leu Phe Gly
            530                 535                 540

Asn Thr Val Asn Leu Thr Ser Arg Thr Glu Thr Thr Gly Glu Lys Gly
545                 550                 555                 560

Lys Ile Asn Val Ser Glu Tyr Thr Tyr Arg Cys Leu Met Ser Pro Glu
                565                 570                 575

Asn Ser Asp Pro Gln Phe His Leu Glu His Arg Gly Pro Val Ser Met
                580                 585                 590

Lys Gly Lys Lys Glu Pro Met Gln Val Trp Phe Leu Ser Arg Lys Asn
            595                 600                 605

Thr Gly Thr Glu Glu Thr Lys Gln Asp Asp Asp
    610                 615

<210> SEQ ID NO 5
<211> LENGTH: 14
<212> TYPE: PRT
<213> ORGANISM: homo sapiens

<400> SEQUENCE: 5

Phe Thr Pro Arg Ser Arg Glu Glu Leu Pro Pro Asn Phe Pro
1               5                   10

<210> SEQ ID NO 6
<211> LENGTH: 22
<212> TYPE: PRT
<213> ORGANISM: Artificial Sequence
<220> FEATURE:
<223> OTHER INFORMATION: PCR primer

<400> SEQUENCE: 6

Lys Gly Lys Lys Glu Pro Met Gln Val Trp Phe Leu Ser Arg Lys Asn
1               5                   10                  15

Thr Gly Thr Glu Glu Thr
            20
```

```
<210> SEQ ID NO 7
<211> LENGTH: 28
<212> TYPE: DNA
<213> ORGANISM: Artificial Sequence
<220> FEATURE:
<223> OTHER INFORMATION: PCR primer

<400> SEQUENCE: 7
aaaaggatcc atgttctgca cgaagctc                                    28

<210> SEQ ID NO 8
<211> LENGTH: 18
<212> TYPE: DNA
<213> ORGANISM: homo sapiens

<400> SEQUENCE: 8
attatggaag cagggagg                                               18

<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
aaaaggatcc atgtacggat ttgtgaat                                    28

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
atgcgtgatt cctgggtacc                                             20

<210> SEQ ID NO 11
<211> LENGTH: 18
<212> TYPE: PRT
<213> ORGANISM: Artificial Sequence
<220> FEATURE:
<223> OTHER INFORMATION: conserved guanylyl cyclase sequence

<400> SEQUENCE: 11

Val Tyr Lys Val Glu Thr Val Gly Asp Lys Tyr Met Thr Val Ser Gly
  1               5                  10                  15

Leu Pro

<210> SEQ ID NO 12
<211> LENGTH: 13
<212> TYPE: PRT
<213> ORGANISM: homo sapiens

<400> SEQUENCE: 12

Tyr Gly Pro Glu Val Trp Glu Asp Ile Lys Lys Glu Ala
  1               5                  10

<210> SEQ ID NO 13
<211> LENGTH: 19
<212> TYPE: PRT
<213> ORGANISM: Artificial Sequence
<220> FEATURE:
<223> OTHER INFORMATION: Conserved guanylyl cyclase sequence
```

```
<400> SEQUENCE: 13

Lys Lys Asp Val Glu Glu Ala Asn Ala Asn Phe Leu Gly Lys Ala Ser
 1               5                  10                  15

Gly Ile Asp

<210> SEQ ID NO 14
<211> LENGTH: 15
<212> TYPE: PRT
<213> ORGANISM: Bos taurus

<400> SEQUENCE: 14

Ser Arg Lys Asn Thr Gly Thr Glu Glu Thr Glu Gln Asp Glu Asn
 1               5                  10                  15

<210> SEQ ID NO 15
<211> LENGTH: 47
<212> TYPE: DNA
<213> ORGANISM: Artificial Sequence
<220> FEATURE:
<223> OTHER INFORMATION: cloning site

<400> SEQUENCE: 15
cggatcccgg gtaccttcta gaattccgga gcggccgctg cagatct                47

<210> SEQ ID NO 16
<211> LENGTH: 46
<212> TYPE: DNA
<213> ORGANISM: Artificial Sequence
<220> FEATURE:
<223> OTHER INFORMATION: cloning site

<400> SEQUENCE: 16
cctagggccc atggaagatc ttaaggcctc gccggcgacg tctaga                 46

<210> SEQ ID NO 17
<211> LENGTH: 38
<212> TYPE: DNA
<213> ORGANISM: homo sapiens

<400> SEQUENCE: 17
ctggtccgcg tggatccccg ggaattcatc gtgactga                          38

<210> SEQ ID NO 18
<211> LENGTH: 15
<212> TYPE: PRT
<213> ORGANISM: homo sapiens

<400> SEQUENCE: 18

Leu Val Pro Arg Gly Ser Pro Gly Ile His Arg Asp Ser Thr Pro
 1               5                  10                  15

<210> SEQ ID NO 19
<211> LENGTH: 6
<212> TYPE: PRT
<213> ORGANISM: Homo sapiens

<400> SEQUENCE: 19

Leu Val Pro Arg Cys Ser
 1               5
```

ISOLATED AND PURIFIED HUMAN SOLUBLE GUANYLYL CYCLASE α1/β1 (HSGCα1/β1)

This application is the National Stage of PCT/DE99/02601 filed on Aug. 16, 1999.

THE TECHNICAL FIELD OF THE INVENTION

The present invention relates to the expression of the cDNA clones for the subunits α1 (hsGCα1) and β1 (hsGCβ1) of human soluble quanylyl cyclase and the subsequent purification of the active enzyme and the use thereof, the medical application of the expression of these clones by gene transfer, as well as antibodies to peptides derived from the sequence and the use thereof.

DISCUSSION OF THE STATE OF THE ART

The endogenous NO/cGMP signaling system mediates important functions such as vasodilation, inhibition of platelet aggregation, neurotransmission, and the immune response. In addition, it is involved in the development of various disease states such as ischemia-reperfusion and inflammatory injuries (Schmidt and Walter, 1994). Therefore, the NO/cGMP system has long been an important starting point for the development of novel drugs for the therapy of coronary heart disease, susceptibility to thrombosis, cardiac insufficiency, angina pectoris, cardiac-dependent pulmonary oedema, hypertensive crises, inflammatory states and cardiac infarction. Until now, such therapies have employed various so-called NO donors, e.g. nitroglycerin, that release NO, thereby replacing endogenous NO and activating soluble guanylyl cyclase (sGC) (FIG. 1). sGC forms cGMP, which mediates the effects of the NO/cGMP pathway via various intracellular receptor enzymes. The application of NO donors has two limitations: I) The repeated application of NO donors results in tolerance in the patient, i.e. loss of activity, when reapplied; II) NO reacts with $O_2^-$ to form peroxynitrite, which is cytotoxic and less effective in activating sGC. Thus, direct activation of sGC by novel, non-NO-containing pharmaceuticals for therapy or gene transfer of sGC would be desirable strategies. Non-NO-releasing activators of sGC are potentially lacking tolerance and NO toxitication. Recently, "YC-1" (3-(5'-hydroxymethyl-2'-furyl)-1-benzylindazol) has been described as the first non-NO-releasing activator of sGC in platelets (Ko et al., 1994; Wu et al., 1995). YC-1 also activates purified sGC from bovine lung and potentiates the activation of NO (Friebe et al., 1996). The effect on human sGC has not been investigated. The human isoform of sGC is not yet available for pharmacological screening.

The NO receptor sGC consists of two subunits, α and β, which together form an enzymatically active heterodimer. Three different isoforms of the α and three of the β subunits have been described in the literature, although from different species. The best investigated isoforms, the bovine α1/β1 and the rat α1/β1 isoforms, have particular significance for cardiovascular research. Until recently, a human homologue of the bovine and rat sGC (e.g. sGCα1/sGCβ1 heterodimers) was unknown. cDNA sequences have been published that reportedly correspond to a human sGCα3 and β3 isoform (Giuili et al., 1992). While sGCβ3 showed a high homology to sGCβ1 (bovine/rat), the sGCα3 sequence contained two restricted regions without homology to sGCα1 (bovine/rat), here designated S1 and S2 (FIG. 2). In addition, it was unknown whether sGCα3 and sGCβ3 can form a functional sGC heterodimer and which role the S1 and S2 regions play.

Furthermore, no other human sGC subunit has yet been expressed as a protein. Recently, a sequence designated hsGCα1 was published in the GeneBank (Accession No. U58855) that lacks the sequence differences to sGCα1 from bovine and rat tissues in the regions S1 and S2. In addition, an alternatively spliced product of hsGCβ3 was recently published in the GeneBank (Accession No. AF020340) that was designated by the authors as an alternatively spliced form of hsGCβ1. The physiological significance of this splice variant of hsGCβ1/3 is unclear. Thus, the question arises as to which of these isoforms is responsible for which physiological function in which cell types.

Furthermore, no antibodies to the human sGCα1/β1 are currently available that are monospecific, directed against the human sequences, or that have been shown to be suitable for immunoblots with human tissues. Peptide antibodies reported thus far only partially show these features: Harteneck et al. and Guthmann et al. used a peptide sequence (VYKVETVGDKYMTVSGLP; SEQ ID NO: 11) that is highly conserved in guanylyl cyclases. Therefore, cross-reaction with particulate guanylyl cyclases (e.g. GC-C) can be expected. Guthmann et al. used a peptide sequence (YGPEVWEDIKKEA; SEQ ID NO: 12) identical to hsGCβ1 and a peptide sequence (KKDVEEANANFLGKASGID; SEQ ID NO: 13) identical to hsGCα1 except for two amino acid exchanges. However, the function of these antibodies in immunoblots was only shown for enriched hsGC from human platelets. In addition, the antisera to hsGCα1 detect a second, unspecific product. Humbert et al. and Koesling et al. used a peptide sequence (SRKNTGTEETEQDEN; SEQ ID NO: 14) of bovine sGCβ1 that partially (amino acids 1–10) overlaps with the peptide used here for the human sGCβ1 (amino acids 13–22) and is identical in this region. The C-terminus of this bovine peptide (amino acids 11–15), however, is clearly different from the human sequence. On the other hand, the antiserum to this peptide was not tested with a human protein but rather only used for immunoprecipitation of the bovine sGC.

Thus, for the human isoform α1/β1 which is important for cardiovascular research, neither native protein nor recombinant protein, nor a one-step purification protocol, nor specific antibodies have been available. An approach for gene therapy (e.g. with adenoviruses or the like) has also not been described yet.

THE TECHNICAL PROBLEM OF THE INVENTION

The NO-independent activation of the human sGCα1/β1 is a promising approach to finding novel drugs or gene transfer techniques for cardiovascular therapy that neither result in tolerance in the patient nor form cytotoxic peroxynitrite. To find such pharmaceuticals, a mass screening for suitable active substances is necessary. Such a pharmacological screening for specific activators or inhibitors via animal testing is too expensive and is not reasonable due to species differences, possible side effects, and effects on other isoforms. Cell culture systems have the disadvantage that only with substantial additional effort can it be determined at which points of the signaling cascade substances are effective. In addition, cell culture is expensive and touchy. The purification of a protein from animal tissues is labor-intensive and results in a low yield. More importantly, because of species differences the results of such a screening are not generally transferable. Here, in particular, the question arises of the significance of the isoforms hsGCα1 and hsGCα3 and whether hsGCβ3 in fact corresponds to a human hsGCβ1. This is an important factor to consider in selecting the appropriate target protein for pharmacological screening or gene therapy. For optimal screening, the human homologue of the protein sGCα1/β1 would have to be purified in large amounts and to be available at low cost. A purification of large amounts of human native sGCα1/β1 protein from human tissues is not possible. Thus, other methods are needed for the drug screening protocol. In addition, no purified antibodies are available for the detection of human sGCα1/β1 that have been shown to be suitable for diagnostic uses, e.g. in normal immunoblotting, ELISA, RIA, or EIA, among other techniques. An approach for the artificial expression of hsGC by gene transfer in humans that could be used therapeutically is also not available.

Therefore, the present invention is based on the technical problem of providing isolated and purified human sGCα1/β1 as well as a process for its production and purification. In addition, a further technical problem of the present invention is to provide antibodies directed against human sGCα1/β1. A further technical problem is the provision of expression vectors containing the cDNA of human sGCα1/β1 based on adenoviruses. Finally, the technical problem of the present invention is the provision of human sGCα1/β1 in purified form and in manageable amounts for drug screening assays aimed at detecting modulators, inhibitors, and activators of human sGCα1/β1.

THE SOLUTION OF THE TECHNICAL PROBLEM

The solution to the above technical problem is provided by the subject-matter of the claims and the following description of the invention.

An object of the invention is a human soluble guanylyl cyclase α1/β1 (hsGCα1/β1) in an isolated form purified to apparent homogeneity.

Another object of the invention is a process for the production of subunit α1 and/or β1 of human soluble guanylyl cyclase comprising the expression of expression vectors containing the DNA sequence for hsGCα1 and/or hsGCβ1 in prokaryotic and eukaryotic host cells, and obtaining of the subunit or subunits.

In a preferred embodiment of the process of the present invention for the production of subunit α1 and/or β1 of human soluble guanylyl cyclase, the step of obtaining the subunit or subunits comprises the lysis of cells, affinity chromatography of the cell lysate, and finally, the elution of the subunit or subunits.

In a further preferred embodiment of the process of the present invention for the production of subunit α1 and/or β1 of human soluble guanylyl cyclase, the expression vector contains additionally at least one DNA sequence of a domain for specific affinity chromatography (affinity tag) with attached protease cleavage site.

Another object of the present invention is a process for the production of human soluble guanylyl cyclase α1/β1 (hsGCα1/β1) comprising the separate expression of an expression vector containing the DNA sequence for hsGCα1 or hsGCβ1 in prokaryotic or eukaryotic host cells, obtaining the subunits, and combining the subunits hsGCα1 and hsGCβ1 into the dimeric guanylyl cyclase α1/β1 (hsGCα1/β1).

A further preferred embodiment of the process of the present invention for the production of human soluble guanylyl cyclase α1/β1 (hsGCα1/β1) also comprises the coexpression of the DNA sequences for hsGCα1 and hsGCβ1 in prokaryotic or eukaryotic host cells, the lysis of the cells containing hsGCα1 and hsGCβ1, affinity chromatography, and the subsequent elution of hsGCα1/β1.

Another object of the present invention is the use of a nucleic acid sequence that codes for subunits hsGCα1 and/or hsGCβ1 of human soluble guanylyl cyclase α1/β1 for somatic gene therapy, particularly for the prevention and therapy of atherosclerosis and its complications, restenosis, ischemia (infarction), peripheral occlusive diseases, and arterial hypertension, as well as, in patients with risk factors for atherosclerosis.

In a particularly preferred embodiment, adenoviral vectors containing hsGCα1 or hsGCβ1 cDNA are used in somatic gene therapy. Other vector systems, however, can also be applied for gene therapeutic, medicinal use.

The methods of gene transfer described in the present invention can also be used for gene transfer of human soluble guanylyl cyclase α2 (GeneBank: x63282) and of the human homologue of soluble guanylyl cyclase β2 (from rat; GeneBank: m57507) as well as for other human soluble guanylyl cyclases.

Another object of the present invention relates to antibodies to human soluble guanylyl cyclase α1/β1 (hsGCα1/β1), obtainable by immunization of a mammal with hsGCα1/β1, either of subunits α1 or β1, or immunogenic peptide fragments thereof, as well as isolation of the antibodies.

THE FIGURES SHOW

FIG. 1 shows various possibilities of modulation of soluble guanylyl cyclase (CsGC-α1/sGC-β1). Normal activation is mediated by NO synthase (NOS) and NO. NO, however, reacts with oxygen radicals to form peroxynitrite (ONOO$^-$), which is cytotoxic and only poorly activates sGC. NO can also be released by NO donors such as nitroglycerin or sodium nitroprusside. sGC can be directly activated by modulators of sGC (e.g. YC-1); alternatively, the activation by NO of sGC is potentiated by these modulators. Additionally, sGC can be overexpressed by use of gene transfer (e.g. using adenoviral vectors) or a pathologically low expression level of sGC can be compensated. Adenoviral (or other) vectors with mutated sGC that has a higher basal activity can also be used. Thus, an elevated cGMP level could be achieved permanently independent of NOS, NO, NO donors, or sGC modulators.

FIG. 2 shows a schematic comparison of the bovine and rat sGCα1 subunits together with the published sequence of the human cDNA clone termed 'sGCα3' (Giuili et al., 1992). The bars represent the protein. 'N' represents the N-terminus and 'C' the C-terminus. The functional segments 'regulatory domain', 'sGC homology domain', and 'cyclase domain' of these proteins are marked with different patterns. The regions 'S1' and 'S2' for which no homologous regions are found in the bovine and rat sGCα1 proteins are marked in black.

FIG. 3 shows a schematic illustration of the human sGCα3 clone with the sequence errors published (Giuili et al., 1992). The cDNA is shown above: the bar represents the coding region of the cDNA, the lines left and right of the bar represent the 5' and 3' untranslated regions, respectively. 'S1' and 'S2' represent the regions that have no homology to the bovine and rat isoforms of sGCα1 (see FIG. 2). The positions of the sequence errors are marked below: line a shows the nucleotide insertions, line b the deletion, and line c the exchanges. A base-pair (bp) scale is shown below. The sequence errors for each of the 3 lines a, b, and c are listed at the bottom: the letter specifies the type of the base concerned, and the number its position in the cDNA.

FIG. 4 shows the verification of the expression of human sGCα1 (A) and sGCβ1 (B) in human tissues by means of PCR using cDNA libraries. Shown is a photo of an ethidium bromidestained agarose gel under UV light with separated PCR products. The arrow on the left points to the specific product. The PCR primers are visible at the bottom of the photo. The tissues from which the cDNA libraries were produced are indicated at the top. No cDNA was added in the negative control, and in the positive control, plasmid containing the cDNA of hsGCα1 was added.

FIGS. 5 and 6 show the baculovirus transfer vectors pVL1393 and pAcG2T, respectively (both without the hsGC cDNA), which were used for the construction of recombinant baculoviruses for the expression of human sGCα1/β1 in Sf9 cells. The circular plasmid with the restriction sites (short names and position in base pairs), the gene for ampicillin resistance ($Amp^R$), the 'origin of replication' (ColE ori), the polyhedrin promotor, the glutathione-S-transfease sequence (only in FIG. 6), and the multiple cloning site (MCS) are shown at the top of the figures. FIG. 5 shows the multiple cloning site with its unique restriction sites at the bottom (upper DNA strand=SEQ ID NO: 15; lower DNA strand=SEQ ID NO: 16). FIG. 6 shows the multiple cloning site with the unique restriction sites as well as a thrombin cleavage site at the bottom (DNA sequence= SEQ ID NO: 17; amino acid sequence=SEQ ID NO: 18, thrombin cleavage site amino acid sequence=SEQ ID NO: 19).

FIG. 7 shows the construction of the plasmids hsGCβ1-pVL1393 (without GST-tag) with the hsGCβ1 cDNA, which was used to obtain genetically modified, hsGCβ1-expressing baculovirus by homologous recombination. The procedure for the plasmid pAcG2T-hsGCβ1 (with GST-tag= glutathione-S-transferase cDNA from *Schistosoma japonicum*) is identical. A fragment was produced that carries an additional BamHI-site at its 5' end by means of PCR with the primers A (bases 89–116 of the hsGCβ1 cDNA+BamHI site at its 5' end; SEQ ID NO: 9) and B (bases 692–711 of SEQ ID NO: 3, the hsGCβ1 cDNA [noncoding strand] with natural KpnI site). Due to the additional restriction sites, fragment 1 (PCR fragment with new BamHI site) and fragment 2 (hsGCβ1 cDNA from KpnI site to EcoRI site) could be inserted together into the BamHI and EcoRI sites of the plasmid pVLI 393. Thus, the complete hsGCβ1 cDNA is under the control of the polyhedrin promotor (PHP).

FIG. 8 shows the construction of the plasmid hsGCα1-pVL1393 (without GST-tag) with the hsGCα1 cDNA which was used to obtain genetically modified, hsGCα1-expressing baculovirus by homologous recombination. The procedure for the plasmid pAcG2T-hsGCα1 (with GST-tag= glutathione-S-transferase cDNA from *Schistosoma japonicum*) is identical. A fragment was produced that carries an additional BamHI site at its 5' end and a natural BsaAI site within the sequence by means of PCR with the primers C (bases 524–541 of the hsGCα1 cDNA+BamHI site at its 5' end; SEQ ID NO: 7) and D (bases 1232–1249 of SEQ ID NO: 1, the hsGCα1 cDNA-[noncoding strand]). Due to the added restriction site, fragment 3 cut with BsaAI (PCR fragment with new BamHI site to the BsaAI site) and fragment 4 (hsGCα1 cDNA from BsaAI site to EcoRI site) could be inserted together into the BamHI and EcoRI sites of the plasmid pVL1393. Thus, the complete hsGCα1 cDNA is under the control of the polyhedrin promotor (PHP).

FIG. 9 shows the verification of the expression of hsGCα1/β1 in Sf9 cells, which were infected with the genetically modified viruses described above (with hsGCα1 or hsGCβ1 cDNA; both without GST-tag=glutathione-S-transferase cDNA from *Schistosoma japonicum*). On the left (A) a Coomassie-stained 10% SDS-polyacrylamide gel is shown on which were loaded the cell homogenates that had been separated into pellet (P) and supernatant (S) by centrifugation (20,000×g). 'Co' designates the control with noninfected Sf9 cells. 'α1' disignates Sfg cells that were infected with viruses containing the hsGCα1 cDNA, and 'β1' designates Sf9 cells that were infected with viruses containing the hsGCβ1 cDNA. The position of hsGCα1 and hsGCβ1 in the gel are marked (α1 or β1). On the right an immunoblot is shown with supernatant (S) and pellet (P) of the cell homogenate from Sf9 cells that were either noninfected (Co) or coinfected with hsGCα1 and hsGCβ1 baculoviruses (α1+β1). The peptide antibodies to hsGCβ1 described above (anti-hsGCβ1) were used in immunoblotting first (FIG. 9B. lines 1–4). Afterwards, the blot was redeveloped with the peptide antibodies to hsGCα1 (anti-hsGCα1; FIG. 9B, lanes 5–8), which additionally revealed the hsGCβ1 bands.

FIG. 10 shows the activity of guanylyl cyclase (formation of CGMP from GTP) in intact Sf9 cells that were coinfected with the genetically modified baculoviruses containing hsGCα1 and hsGCβ1 CDNA described here (both without GST-tag). Shown is the content of cGMP in pmol per $10^6$ cells with different treatments, indicated at the bottom of the figure. Sample 1 is untreated in both panels A and B. 1 mM IBMX (3-isobutyl-1-methylxanthine) was added to each of the other samples (top line: black crossbar). In the middle line, the concentration of SNP added to the samples is indicated in $\mu M$. The bottom line shows the concentration of added YC-1 (A, left) or ODQ (B, right) in $\mu M$.
YC-1=3-(5'-hydroxymethyl-2'-furyl)-1-benzylindazol;
ODQ=1H-[1,2,4]oxadiazolo[4,3,-a]chinoxalin-1-on;
SNP=sodium nitroprusside;
cGMP=cyclic 3', 5'-guanosine monophosphate FIG. 11 shows the activity of guanylyl cyclase (formation of cGMP from GTP) in homogenates of Sf9 cells that were coinfected with the genetically modified baculoviruses containing hsGCα1 and hsGCβ1 cDNA described here (both without GST-tag). As shown at the top, (A), the soluble cell fraction (supernatant after centrifugation at 20,000×g) was used, and at the bottom, (B), the respective pellet. In each case, the amount of cGMP formed in pmol per mg protein per minute is shown for homogenates of cells that were harvested at different time points (indicated in hours) after infection with the baculoviruses. cGMP formation was measured with (black boxes) and without (white boxes) the addition of 100 $\mu M$ SNP.

FIG. 12 shows the activity of guanylyl cyclase (formation of cGMP from GTP) in Sf9 cells that were coinfected with the genetically modified baculoviruses containing hsGCβ1 cDNA (without GST-tag) and hsGCα1 cDNA (with GST-tag=glutathione-S-transferase cDNA from *Schistosoma japonicum*). The formation of cGMP in pmol per mg protein per minute during the purification procedure (affinity chromatography on glutathione sepharose 4B) is shown. In each case, activity was measured in the lysate (after removing the insoluble part by centrifugation at 20,000×g), in the supernatant after binding of hsGC to glutathione sepharose 4B (flow-through), in both supernatants of the washes of hsGC bound to glutathione sepharose 4B (1. and 2. wash), as well as in the supernatant after elution of hsGC with reduced glutathione (1. and 2. elution). The formation of cGMP was determined without (black boxes, 'basal') and with (grey boxes, '+100 $\mu M$ SNP') addition of 100 $\mu M$ SNP.

FIG. 13 shows the natural, endogenous expression of hsGCα1 and hsGCβ1 in different human tissues in an immunoblot. The peptide antibodies to hsGCα1 described above (anti-hsGCα1) were used on the left (A), and the peptide antibodies to hsGCβ1 (anti-hsGCβ1) were used on the right (B). On the right, the peptide to which the antibodies were raised was added as negative control (peptide:+), while no peptide was added on the left (peptide:−). The SDS extracts of rhsGCα1-(in panel A of the figure) or rhsGCβ1-overexpressing Sf9 cells (in panel B of the figure) (Sf9), of human cerebral cortex (cortex), of human cerebellum (cerebellum), and of human lung (lung) were loaded on an 8% polyacrylamide gel. The specific bands of hsGCα1 (α1) and hsGcβ1 (β1) are indicated by an arrow.

FIG. 14 shows in immunoblots the purification of hsGCα1 (as a hsGCα1/hsGCβ1 dimer) from Sf9 cells that were coinfected with the genetically modified baculoviruses containing hsGCα1 cDNA with GST-tag (=glutathione-S-transferase cDNA from *Schistosoma japonicum*) and hsGCβ1 CDNA (without GST-tag). Cell lysate was incubated with glutathione sepharose 4B, and after binding, the supernatant was loaded (supernatant after binding). The sepharose was washed twice and the respective supernatants of this wash were loaded (1. and 2. wash). Subsequently, elution was performed by cleavage of the hsGCα1 protein from the GST-tag with thrombin and an aliquot was loaded ('elution with thrombin'). Then, SDS stop buffer was added to the glutathione sepharose 4B and an aliquot was loaded (GSH sepharose after elution). In addition, glutathione sepharose 4B with bound hsGCα1 without prior thrombin elution to which SDS buffer had been added was loaded (GSH sepharose before elution). The immunoblot was developed with the affinity-purified peptide antibodies to the C-terminus of hsGCα1 described here. The arrows on the right point to the specific bands of hsGCα1 with the GST-tag (GST-hsGCα1) and hsGCα1 without the GST-tag (hsGCα1).

FIG. 15 shows the purification of hsGCα1/β1 from Sf9 cells that were coinfected with the genetically modified baculoviruses containing hsGCα1 cDNA with GST-tag (=glutathione-S-transferase cDNA from *Schistosoma japonicum*) and hsGCβ1 cDNA without GST-tag in a Coomassie Brilliant Blue R250-stained SDS-polyacrylamide gel. Cell lysate of these infected Sf9 cells (lysate) was incubated with glutathione sepharose 4B, and the supernatant loaded after the binding (supernatant after binding). The glutathione sepharose 4B was washed twice and the respective supernatants of this wash buffer were loaded (1. and 2. wash). In one sample, the bound GST-hsGCα1/β1 was eluted by incubation with reduced glutathione and loaded (elution with glutathione). In the other samples, the glutathione sepharose was washed with the buffer for the thrombin cleavage—without thrombin—and the supernatant of this buffer was loaded (3. wash). Then, the hsGCα1/β1 dimer was eluted by incubation with different amounts of thrombin and the eluates were loaded (elution with 0.25–1 U/ml thrombin) [U=unit]. The same relative amount of each of the samples was used. The bands visible with the different elution methods are indicated on the right: GST-hsGCα1= hsGCα1 with GST-tag; hsGCα1=hsGCα1 without GST-tag; hsGCβ1=hsGCβ1 without GST-tag. On the left are the molecular weight standards loaded on the gel, the size of which (in kDa) is indicated on the far left side.

FIG. 16 shows the construction of the recombinant adenoviral hsGC vectors. The cDNAs of hsGCα1 and hsGCβ1 (grey bars) were inserted in the adenoviral transfer plasmid pZS2, which has a deletion in the adenovirus E1 region (ΔE1) and a unique XbaI site in this plasmid. This resulted in the plasmids hsGCα1-pZS2 and hsGCβ1-pZS2, respectively. hsGCα1-pZS2 and hsGCβ1-pZS2 cut with the restriction enzyme XbaI (middle bar, indicated as 'sGCpZS2') were ligated into the XbaI site of the long arm (upper bar, 'RR5') of Ad5. This resulted in the adenovectors Ad5CMVhsGCα1 and Ad5CMVhsGCβ1, respectively (lower bar, 'Ad 5 CMV sGC') in which the sGC cDNAs lie under the control of the CMV promotor and CMV enhancer (CMV=cytomegalovirus).

FIG. 17 shows the stimulation of sGC activity by 100 μM SNP (=sodium nitroprusside) in EA.hy926 cells that were coinfected with both hsGC adenoviruses Ad5CMVhsGCα1 and Ad5CMVhsGCβ1 (samples A–C) and in noninfected EA.hy926 cells (sample D). The amount of pmol cGMP formed per mg protein per minute is plotted on the Y axis. The dark bars represent basal cGMP formation without SNP stimulation, and the light bars represent cGMP formation with SNP stimulation.

FIG. 18 shows the DNA sequence of human soluble guanylyl cyclase α1 (hsGCα1); SEQ ID NO: 1.

FIG. 19 shows the amino acid sequence of human soluble guanylyl cyclase α1 (hsGCα1); SEQ ID NO: 2.

FIG. 20 shows the DNA sequence of human soluble guanylyl cyclase β1 (hsGCβ1); SEQ ID NO: 3.

FIG. 21 shows the amino acid sequence of human soluble guanylyl cyclase β1 (hsGCβ1); SEQ ID NO: 4.

FIG. 22 shows the amino acid sequence of the peptide that was used for the production of antibodies to human soluble guanylyl cyclase α1 (hsGCα1) (corresponds to amino acids 634–647 of hsGCα1); SEQ ID NO: 5.

FIG. 23 shows the amino acid sequence of the peptide that was used for the production of antibodies to human soluble guanylyl cyclase β1 (hsGCβ1) (corresponds to amino acids 593–614 of hsGCβ1); SEQ ID NO: 6.

Figure 1:
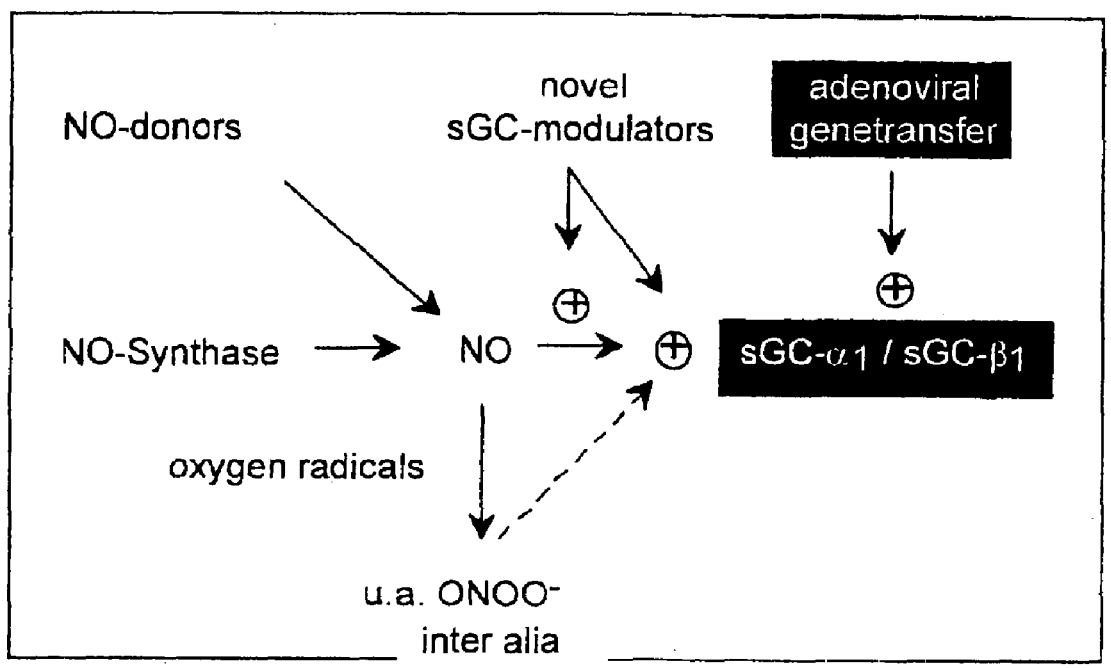
Figure 2:
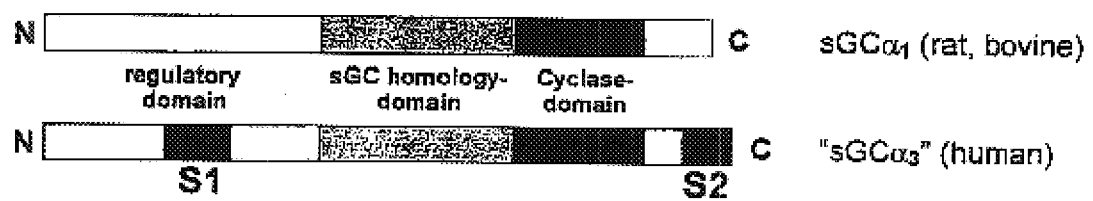

FIG. 24 shows the DNA sequence of the PCR primer pair for human soluble guanylyl cyclase α1 (hsGCα1). Upper primer (corresponds to nucleotides 524–541 of the hsGCα1 cDNA sequence with added BamHI restriction site); SEQ ID NO: 7. Lower primer (corresponds to nucleotides 1249–1232 of the hsGCα1 cDNA sequence [noncoding strand]); SEQ ID NO: 8.

FIG. 25 shows the DNA sequence of the PCR primer pair for human soluble guanylyl cyclase β1 (hsGCβ1). Upper primer (corresponds to nucleotides 89–106 of the hsGCβ1 CDNA sequence with added BamHI restriction site); SEQ ID NO: 9. Lower primer (corresponds to nucleotides 692–711 of the hsGCβ1 cDNA sequence [noncoding strand]); SEQ ID NO: 10.

ADVANTAGES OF THE PRESENT INVENTION AND SOLUTION OF THE ABOVE-MENTIONED TECHNICAL PROBLEMS ACCORDING TO THE PRESENT INVENTION

1.) The cDNA clones described in the literature as sGCα3 and sGCβ3 were identified as human homologues of bovine and rat sGCα1 and sGCβ1, and in the following are termed human sGCα1 (hsGCα1) and human sGCβ1 (hsGCβ1). According to present knowledge, this sGCα1/β1 isoform is pharmacologically more important due to its function in the cardiovascular system. Because the original clone of hsGCα3 was examined, it could be shown that hsGCα1 and hsGCα3 do not exist in parallel but rather only the form hsGCα1. Thus, an obvious target protein for pharmacological mass screening and gene therapy has been identified.

2.) With the methods described by the present invention, a functional, active expression of human sGC has been obtained for the first time. Thus, the respective protein can be produced by genetic methods for the first time.

By use of the peptide antibodies to sGC of the present invention, it is possible to determine the expression of sGC in human tissues as well as diagnose dysfunctional conditions (if expression of sGC is too high, too low, or absent). In addition, the present invention provides the technical prerequisites needed to further elucidate the control of transcription and translation of hsGC. The peptide antibodies of the invention have the advantage that they are monospecific, directed at the human sequence, and that their suitability for immunoblots with human tissues has been demonstrated. Other peptide antibodies exhibit these features only partially: Harteneck et al. and Guthmann et al. used a peptide sequence (VYKVETVGDKYMTVSGLP; SEQ ID NO: 11) that is relatively highly conserved in guanylyl cyclases. Thus, cross-reaction with particulate guanylyl cyclases (e.g. GC-C) would be expected. Furthermore, Guthmann et al. used a peptide sequence (YGPEVWEDIKKEA; SEQ ID NO: 12) identical to hsGCβ1 and a peptide sequence identical to hsGCα1 except for two amino acid exchanges (KKDVEEANANFLGKASGID: SEQ ID NO: 13), but the function of these antibodies in immunoblotting has only been shown for enriched hsGC from human platelets. In addition, these antibodies to hsGCα1 recognized a second, unspecific product. Humbert et al. and Koesling et al. used a peptide sequence (SRKNTGTEETEQDEN; SEQ ID NO: 14) from bovine sGCβ1 that is in part (amino acids 1–10) identical to the peptide used here (amino acids 13–22) for hsGCβ1, although the C-terminus (amino acids 11–15) differed markedly from that of the human sequence. The antiserum to this peptide, however, has not been tested on human protein and has only been used for immunoprecipitation of bovine sGC.

In addition to the peptides shown in FIGS. 22 and 23 and their immunogenic fragments for the production of the antibodies to hsGCα1 or hsGCβ1 in rabbits of the present invention, the production of monoclonal or polyclonal antibodies to the whole hsGCα1/β1 protein or its cleavage products is possible. Various animal species (preferably mouse, rat, or rabbit) can be used for the production of these antibodies.

4.) By use of the eukaryotic baculovirus/Sf9 expression system of the present invention, human soluble guanylyl cyclase α1/β1 can be produced in high amounts. The attachment of a nucleotide sequence that codes for a polypeptide suitable for affinity chromatography (affinity tag, e.g. glutathione-S-transferase=GST-tag) with an attached protease cleavage site at the N-terminus of the cDNA of the α1 subunit allows the rapid and simple purification of the coexpressed dimeric protein by means of a single affinity chromatographic step. The attached affinity tag is subsequently removed by digestion with a protease. Thus, a protein identical in primary structure to the native protein is obtained. This revolutionary, fast, and clean purification yielding high amounts of very pure, functional human sGC results in new possibilities for a mass screening for specific activators and inhibitors as well as for the pharmacological characterization of potential drugs.

Purification of hsGCα1/1 can also be accomplished by ion exchange chromatography, gel filtration, immunoaffinity chromatography, and other chromatographic procedures, e.g. on ATP-, GTP-. cGMP- or Blue-sepharose, and other similar chromatographic media.

5.) The process of the present invention can also be used for other isoforms of the human, rat, and bovine enzyme in an identical manner. In the process provided in the present invention, various affinity tags (e.g. histidine oligomer) and different expression systems (e.g. E. coli) can be used. Other parts of the hsGCα1 and hsGCβ1 sequences can also be used for the production of antibodies to peptides or the whole protein.

6.) The availability of high amounts of an isolated human protein in high purity and in high quality is essential for modem pharmaceutical development. Until now, this requirement was not fulfilled in the search for alternatives to the classical NO donors. Mass screening for specific activators or inhibitors in animal testing is too expensive and would not make sense due to species differences, possible side effects, and effects on other isoforms. Cell culture systems have the disadvantage of requiring substantial additional effort to determine precisely at which point within the signaling cascades substances act. In addition, cell culture is expensive and touchy. Compared with the expression of a protein using recombinant DNA technology, the purification of a protein from animal tissues is more labor intensive and results in lower yields. In particular, the results of a pharmacological screening can only be generalized to a limited extent because of differences between species. In contrast, processes of the present invention provide for recombinant, inexpensive hsGCα1/β1 in high amounts, and unequivocal predictions concerning modulation, activation, or inhibition of this particular human enzyme can be made from a screening procedure. Species differences and lack of applicability to human are excluded a priori by the use of a human enzyme.

In addition, hsGC is available thereby in high amounts and adequate purity for crystallization and clarification of its structure. Thus, an important prerequisite for rational drug design by means of molecular modeling is fulfilled.

7.) In addition to the use of isolated hsGCα1/β1, intact Sf9 cells that express hsGCα1/β1 by being infected with the recombinant baculoviruses described here can be used in in vitro experiments.

8.) Transient (e.g. with adenoviral vectors) or stable overexpression can be achieved by means of gene transfer. Thus, the cGMP level can be elevated even at low NO concentration or in the case of poor activation of sGC due to peroxynitrite formation. This approach also has conceptional advantages compared to the gene transfer of NOS (NO synthase) because the formation of cytotoxic peroxynitrite, which is, less effective in activating sGC, is circumvented with the approach of the present invention. Furthermore, a permanent increase in the cGMP level could be achieved (e.g. for therapeutic purposes) independently of NOS, NO, NO donors, or sGC modulators by gene transfer of mutated sGC with elevated basal activity.

9.) In addition to the purification procedure for hsGCα1/β1 described here, purification from Sf9 cells is also possible after infection with the described baculoviruses containing hsGCα1 or hsGCβ1 cDNA if coinfection is performed with hsGCα1 baculoviruses without a GST-tag (GST-tag= appended glutathione-S-transferase sequence from *Schistosoma japonicum*) and hsGCβ1 baculoviruses having a GST-tag as well as with hsGCα1 baculoviruses having a GST-tag and hsGCβ1 baculoviruses having a GST-tag.

Furthermore, use of a column containing glutathione sepharose 4B is possible in addition to the use of glutathione sepharose 4B alone in a batch-wise step.

Purification can also be performed by digesting the dimeric fusion protein GST-hsGCα1/β1 with thrombin after elution of the fusion protein from the glutathione sepharose 4B with reduced glutathione. After dialysis (to remove the reduced glutathione), the GST-tag which has been cleaved from the protein can be removed from the mixture by additional affinity chromatography on glutathione sepharose 4B.

10.) The process of the present invention can also be used for human soluble guanylyl cyclase α2 (GeneBank: x63282) and any potentially existing human homologue of the soluble guanylyl cyclase β2 (from rat; GeneBank: m57507) as well as for other human soluble guanylyl cyclases (in all technical variations described in the present invention).

The examples illustrate the present invention.

EXAMPLE 1

The Corrected Sequence of hsGCα1 and hsGCβ1

Figure 3:
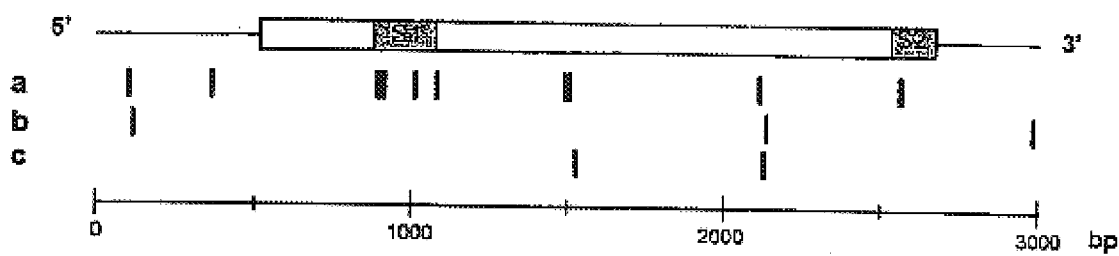

The original clone of the human isoform sGCα3 and sGCβ3 (Giuili et al., 1992) was sequenced again. While the sequence of the sGCβ3 clone was confirmed (see SEQ ID NO: 3 and FIG. 20), the sequencing of sGCα3 showed that the original publication (Giuili et al., 1992) contained 19 sequencing errors, which are summarized in FIG. 3. The corresponding corrected α3-cDNA sequence is shown in SEQ ID NO: 1 and FIG. 18. The deduced amino acid sequence is shown in SEQ ID NO: 2 and FIG. 19. Furthermore, the corrected sequence (see SEQ ID NO: 1 and FIG. 18) is identical with the human sGCα1 sequence published in the GeneBank (accession No. U58855), whereby the 5' untranslated region of the sequence provided here is 506 base pairs longer. Therefore, 'sGCα3' is now classified as human sGCα1 (hsGCα1). Thus, it was shown that two different hsGCα subunits α1 and α3 do not both exist in humans, which could be important for cardiovascular research but rather—in analogy to the situation in bovine and rat tissues—only hsGCα1.

TABLE 1

Revised terminology of soluble guanylyl cyclase cDNAs and proteins and their detection in human tissue.

| | human sGC subunits | |
|---|---|---|
| | α | β |
| isoform 1 | cDNA and protein detectable | cDNA and protein detectable active, when coexpressed |
| isoform 2 | cDNA detectable | active, when coexpressed with bovine β1 |

The expression of sGCα1 and sGCβ1 mRNA in human tissues was demonstrated by means of PCR (FIG. 4). The amplification of a hsGCβ1 fragment with a PCR primer pair (5'-AAAAGGATCCATGTACGGATTTGTGAAT-3'= nucleotides 89–106 of SEQ ID NO: 3, the hsGCβ1 cDNA sequence with added restriction site; 5'-ATGCGTGATTCCTGGGTACC-3'=692–711 of SEQ ID NO: 3, the hsGCβ1 cDNA sequence) with an annealing temperature of 54° C. resulted in one specific band each in cDNA libraries from brain, heart, kidney, lung, pancreas, and skeletal muscle. The identity of the amplified fragment was confirmed by sequencing. The amplification of a hsGCα1 fragment with a PCR primer pair (5'-AAAAGGATCCATGTTCTGCACGAAGCTC-3'= nucleotide 524–541 of SEQ ID NO: 1, the hsGCα1 cDNA sequence with added restriction site; 5'-ATTATGGAAGCAGGGAGG-3'=1249–1232 of SEQ ID NO: 1, the hsGCα1 cDNA sequence) with an annealing temperature of 54° C. resulted in one specific band each in cDNA libraries from heart (FIG. 4A) and lung (not shown). In each case, the sequencing of the fragments resulted in the corrected hsGCα1 sequence; and the 'hsGCα3' sequence published by Giuili et al. was not found. Thus, it was shown that in humans, only one hsGCα1/β1 exists, and that the potential hsGCα3/β3 is a result of sequencing errors. This results in a clear picture for cardiovascular research concerning which sGC isoform should be the target protein for pharmacological screening.

EXAMPLE 2

Construction of Recombinant Baculoviruses for the Expression of Human sGCα and sGCβ in Insect Cells In order to verify that hsGCα1 and hsGCβ1 can form a functional, heterodimeric sGC protein, both cDNAs were inserted into baculoviruses. Using these baculoviruses, the recombinant protein was expressed under the control of the strong polyhedrin promotor in insect cells (Sf9 cells). For the production of the recombinant baculoviruses, the baculovirus transfer vector pVL1393 (Pharmingen, San Diego, Calif., USA; FIG. 5) and the baculovirus transfer vector pAcG2T (with glutathione-S-transferase sequence from *Schistsoma japonicum* and thrombin cleavage site; Pharmingen; FIG. 6) were used in which the foreign genes hsGCα1 and hsGCβ1 were cloned, respectively. The cotransfection of such a recombinant pVL1393 or pAcG2T plasmid with BaculoGold baculovirus DNA (Pharmingen) allowed the direct isolation of the genetically modified baculoviruses with hsGCα1 or hsGCβ1 cDNA formed by homologous recombination from the cell culture media.

Figure 7:
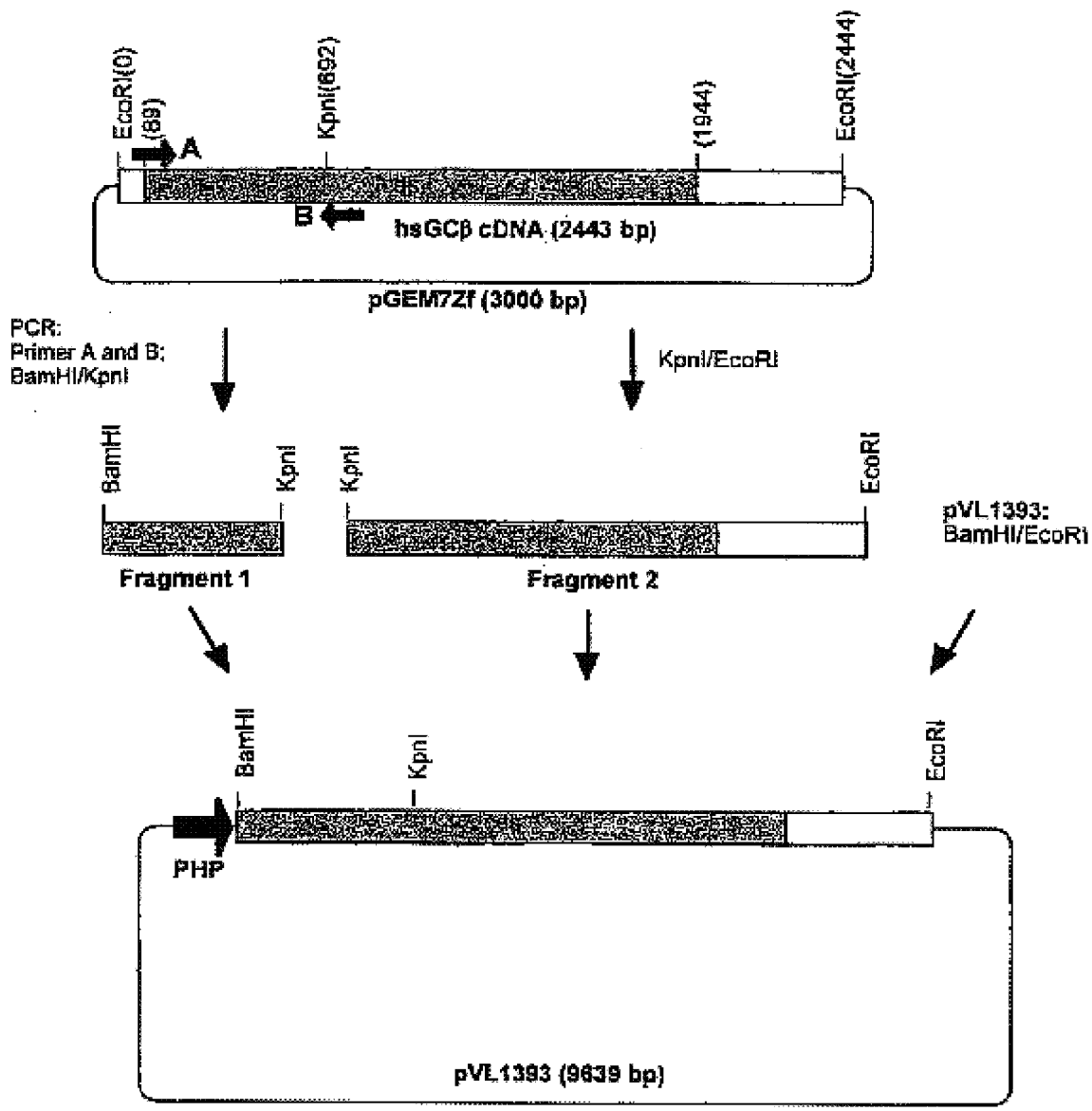

The construction of pVL1393-hsGCβ1 is schematically shown in FIG. 7 (identical procedure for pAcG2T-hsGCβ1). The coding region of the hsGCβ1 cDNA with the 3' untranslated region but without the 5' untranslated region was cloned into pVL1393. For this, a BamHI site was introduced by means of PCR with primers A and B immediately upstream of the codon coding for the start methionine. The thus amplified fragment 1 was digested with BamHI/Kpnl; fragment 2 was isolated from the sGCβ1 cDNA clone with KpnI/EcoRI. Fragments 1 and 2 as well as the vector opened with BamHI and EcoRI were ligated (see FIG. 7).

Figure 8:
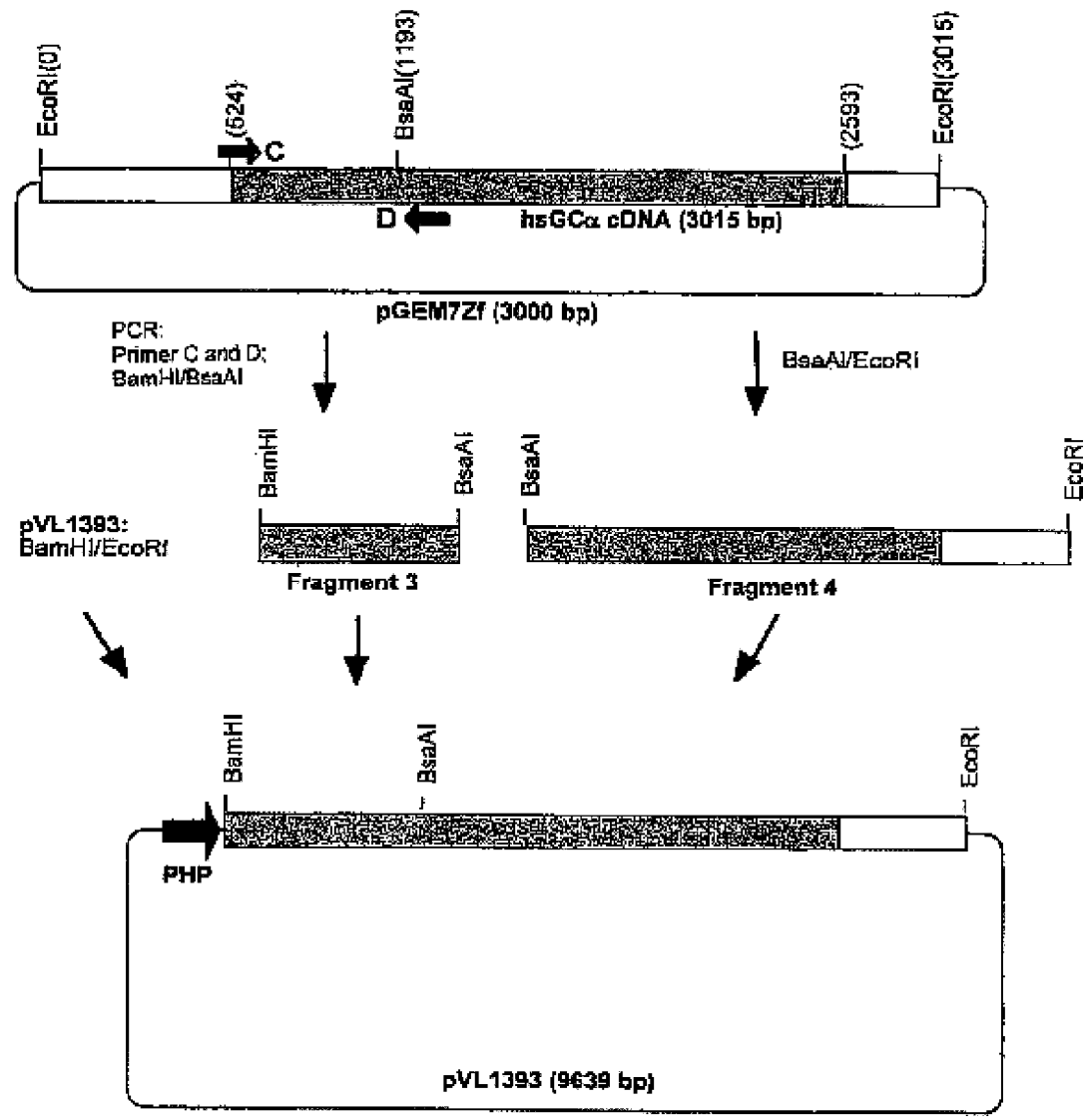

The construction of pVL1393-hsGCα1 is shown schematically in FIG. 8 (identical procedure for pAcG2T-hsGCα1). The coding region of the hsGCα1 cDNA with the 3' untranslated region but without the 5' untranslated region was cloned into pVL1393. For this, a BamHI site was introduced by means of PCR with primers C and D immediately upstream of the codon coding for the start methionine. The thus amplified fragment 3 was digested with BamHI/BsaAI; fragment 4 was isolated from the sGCα1 cDNA clone with BsaAI/EcoRI. Fragments 3 and 4 as well as the vector opened with BamHI and EcoRI were ligated (see FIG. 8).

For the production of the recombinant hsGCα1 and hsGCβ1 baculoviruses, the baculovirus transfer vectors (pVL1393-hsGCα1, pAcG2T-hsGCα1, pVL1393-hsGCβ1, pAcG2T-hsGCβ1) were each cotransfected with baculovirus DNA (BaculoGold; Pharmingen, San Diego, Calif., USA) in monolayers of Sf9 cell cultures.

For this, the cells were cultivated at 27° C. in IPL-41 media (Gibco) supplemented with 10% (vol/vol) fetal calf serum (Biochrom), 4% (vol/vol) tryptose-phosphate-broth (Gibco), 1% (vol/vol) Pluronic F68 (Gibco), 0,5% amphotericin B (Gibco), 80 µg/ml gentamycin sulfate (Gibco), and 0.5 mM δ-aminolevulinic acid (Merck). Recombinant hsGCα1 and hsGCβ1 baculovirus clones were obtained from the culture media by means of plaque purification. For the production of virus stock solutions with high titer, Sf9 shaking cultures (0.5×10$^6$ cell/ml) were infected with a M.O.I. (multiplicity of infection) of 0.1 pfu/cell (pfu=plaque forming units) and harvested 6 days after infection.

EXAMPLE 3

Production of Recombinant hsGCα1 and hsGCβ1 in Sf9 Cells

Figure 9:
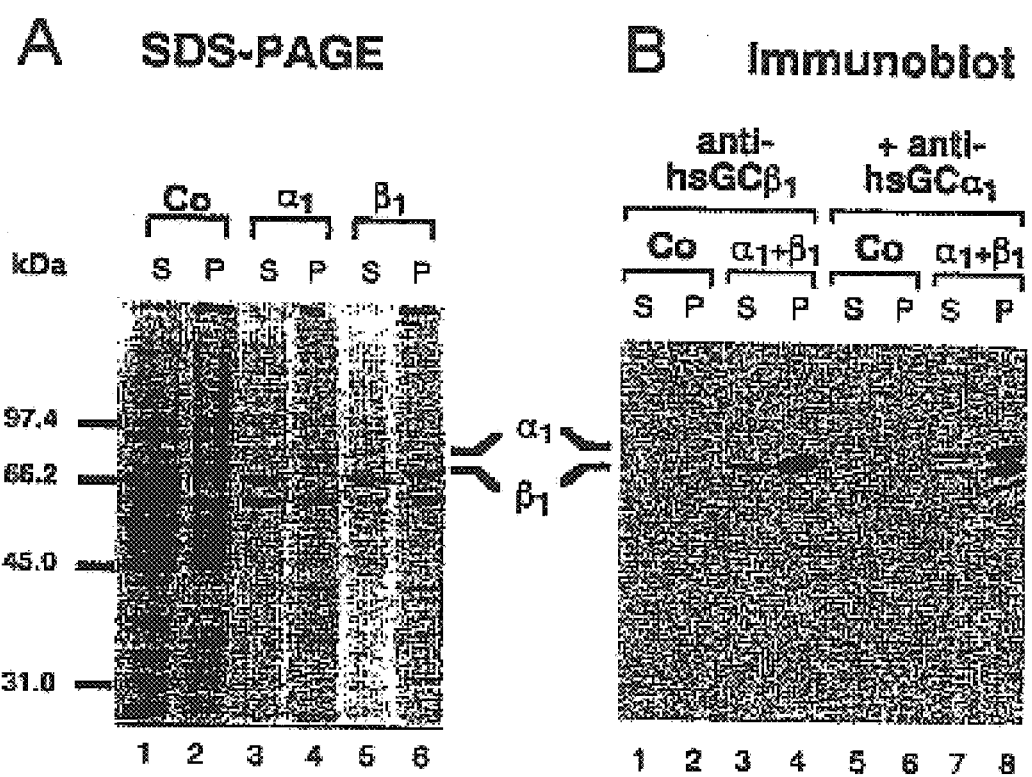

Ten of each recombinant hsGCα1 and hsGCβ1 baculovirus clones were tested for expression of recombinant protein in Sf9 cells. For this, Sf9 monolayer cell cultures were infected with plaque-purified, recombinant hsGCα1 or hsGCβ1 baculoviruses, incubated at 27° C. for 5 days, harvested with a cell scraper, resuspended in 0.5 ml lysis buffer (25 mM TEA, pH 7.8, 50 mM NaCl, 1 mM EDTA, 5 mM DTT, 1 µM leupeptin, 0.5 mg/l trypsin inhibitor), and homogenized by sonication ('Sonifier 250', 'standard'-tip, Branson; 15 times, 'duty cycle': 15%, intensity: 1). After centrifugation of the homogenates at 20,000×g, the supernatant and pellet were analyzed by SDS-PAGE. Three of the hsGCβ1 baculovirus clones and two of the hsGCα1 baculovirus clones yielded recombinant protein in amounts that were visible in the insoluble fraction by staining with Coomassie Brilliant Blue R250. Recombinant human sGCα and sGCβ (rhsGCα and rhsGCβ) migrated with an apparent molecular weight of 79.5 (hsGCα1) and 68.5 kDa (hsGCβ1), which is very close to the predicted molecular weights deduced from the amino acid sequence (77.5 and 70.5 kDa, respectively) (representative clones in FIG. 9). The baculovirus clones that showed the highest expression of recombinant proteins in the immunoblot were used for the expression of functional heterodimeric hsGC [see examples 4–7].

EXAMPLE 4

Recombinant Human sGC in Intact Insect Cells is Active and Stimulated by NO

For the production of functional heterodimeric human sGC, rhsGCα1 and rhsGCβ1 were coexpressed in Sf9 cells with recombinant baculoviruses. For this, Sf9 monolayer cultures [2.5×10$^6$ cells/dish, Ø 90 mm; supplements see example 2] were coinfected with a M.O.I. (multiplicity of infection) of 2 pfu/cell of each recombinant baculovirus (hsGCα1 and hsGCβ1; both without GST-tag) and cultivated for 48 hours at 27° C. The basal as well as the NO-stimulated activity of the sGC in the cells was determined by measurement of the cGMP content in the cells in the presence of the phosphodiesterase inhibitor IBMX (3-isobutyl-1-methylxanthine).

For the determination of the cGMP content, the culture media was replaced by Krebs-Ringer-buffer (KRB; 1.19 mM NaCl; 4.74 mM KCl; 2.54 mM CaCl$_2$; 1.19 mM MgSO$_4$; 1.19 mM KH$_2$PO$_4$; 25 mM NaHCO$_3$; 10 mM HEPES; pH 7.4; 0.1% BSA) which, in addition, contained 1 mM IBMX. The cells were incubated for one hour at 27° C. Then the cells were washed with ice-cold KRP and harvested in 1 ml ice-cold ethanol (80%) with a cell scraper. The cells were homogenized by sonication [see Example 3] and centrifuged at 20,000×g for 20 minutes. The supernatant was dried in a speed-vac and the residue resuspended in 25 mM TEA, pH 7.8. The cGMP content was determined by means of RIA (Biotrend).

Figure 10:
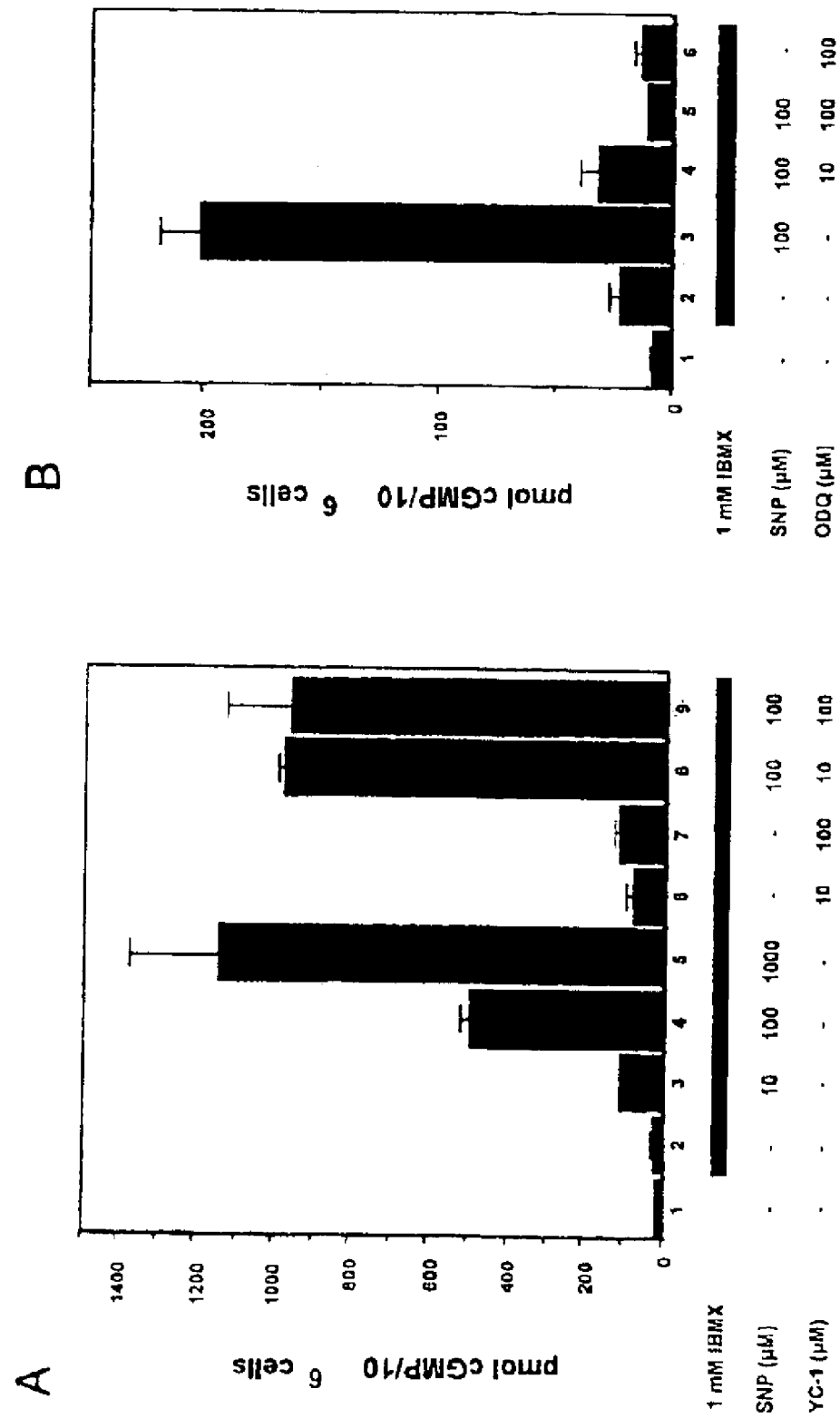

The coexpression of rhsGCα1 and rhsGCβ1 resulted in the formation of functional sGC with basal activity in Sf9 cells (FIG. 10): While noninfected Sf9 cells contained approximately 0.1 pmol cGMP/10$^6$ cells (not shown), approximately 20 pmol cGMP/10$^6$ cells was found in rhsGC-expressing cells (FIG. 10). This basal activity of recombinant hsGC was increased by an NO donor, SNP (sodium nitroprusside). When the cells were incubated with 10, 100, or 1000 µM SNP for 2 minutes prior to the harvest, the cGMP content increased in a concentration-dependent manner by up to 50 fold (FIG. 10).

EXAMPLE 5

Figure 11:
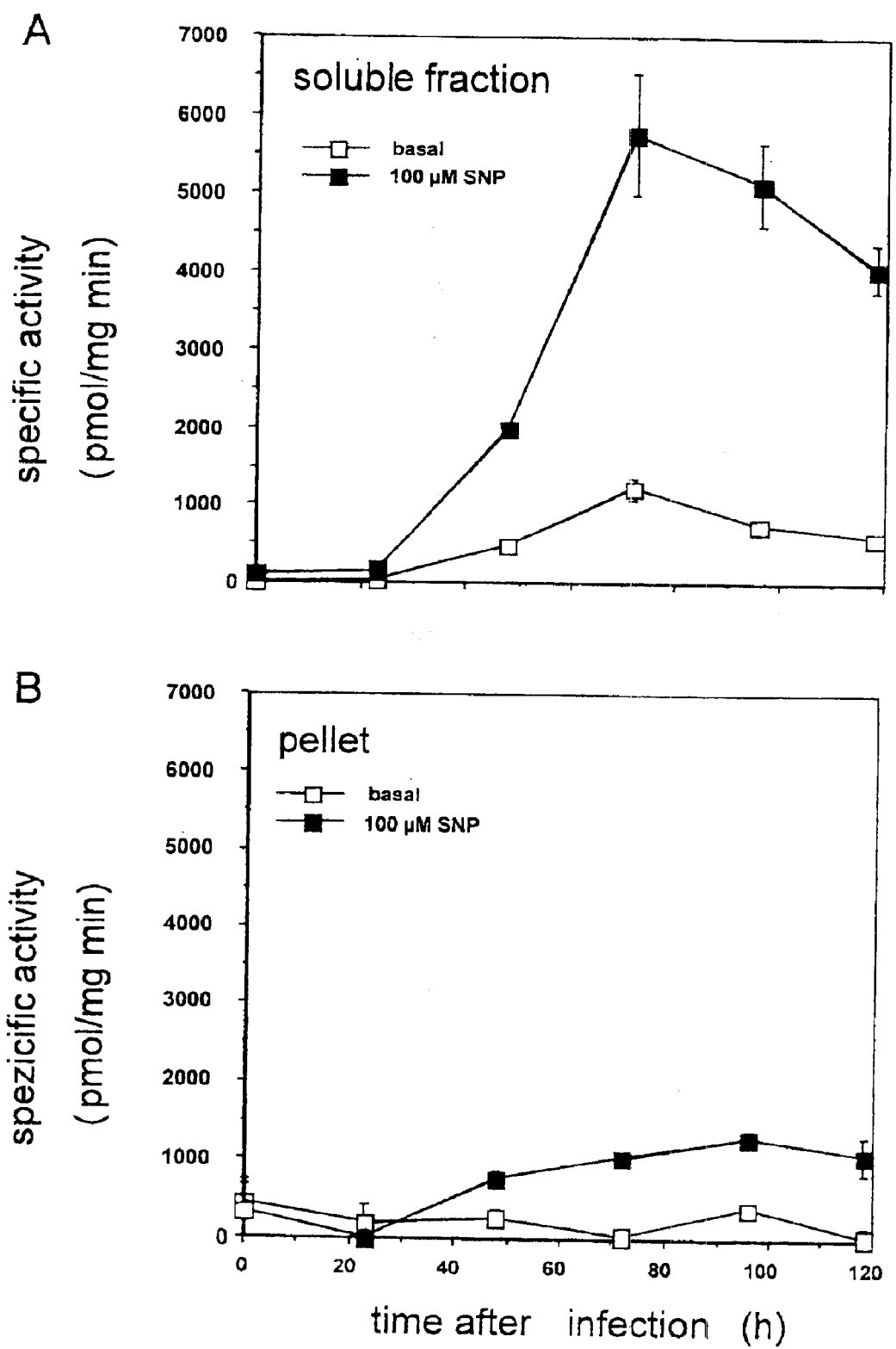

Recombinant Human sGC in Insect Cell Extracts is Active and Stimulated by NO The activity of the recombinant hsGC (after expression with the recombinant baculoviruses described above) was not only determined in intact Sf9 cells but also in Sf9 cell extracts. For the production of such extracts, Sf9 shaking cultures [2×10$^6$ cells/ml; supplements see Example 2] were coinfected with a M.O.I. (multiplicity of infection) of 1 pfu/cell of each virus (hsGCα1 and hsGCβ1; both without GST-tag) and incubated at 27° C. Samples were taken (4 ml) at 0, 24, 48, 72, 96, and 118 hours after infection, the cells sedimented, resuspended in 1 ml lysis buffer and homogenized by sonication [see Example 3]. The homogenates were centrifuged at 20,000×g for 15 minutes and the insoluble pellet was resuspended again in lysis buffer. The samples were adjusted to 50% glycerin (vol/vol) and stored at −20° C. The protein concentration was determined spectrophotometrically with the standard method of Bradford (Bradford, 1976). The sGC activity was determined by the formation of [$^{32}$P]cGMP from [α$^{32}$P]GTP (Schultz and Böhme, 1984). The reactions contained 50 mM TEA (pH 7.4), 3 mM MgCl$_2$, 3 mM DTT, 1 mM IBMX, 1 mM cGMP, 5 mM creatine phosphate, 0.25 mg/ml creatine kinase, and 500 µM GTP in a total volume of 100 µl. After incubation at 37° C. for 10 minutes, the reaction was started by simultaneous addition of cell extract and the sGC activators SNP, CO, or YC-1. The [$^{32}$P]cGMP formed was measured as described (Schultz and Böhme, 1984). Basal rhsGC activity (i.e. cGMP formation by rshGC without activation of the enzyme by addition of NO or other activators), mainly found in the soluble Sf9 cell fraction (FIG. 11A), reached is maximum 72 hours after infection of the cells and was increased up to 5 fold with 100 µM SNP (FIG. 11A). The pellet fraction did not contain measurable basal sGC activity at any time point; although in the presence of SNP a low degree of sGC activity was found (FIG. 11B).

EXAMPLE 6

Influence of YC-1 and ODQ on Recombinant Human sGC

YC-b 1(3-(5'-hydroxymethyl-2'-furyl)-1-benzylindazol) and ODQ (1H-[1,2,4]oxadiazol[4,3,-a]chinoxalin-1-on) are substances that were described to specifically influence the activity of sGC. Thus, it was investigated if this also holds true for rhsGC.

After expression with the recombinant baculoviruses (without GST-tag) described above, rhsGC was activated in intact Sf9 cells by YC-1. The NO-potentiating effect was also found: the cGMP content of cells expressing rhsGC was increased 3.4 fold by incubation with 10 μM YC-1 for 2 minutes (FIG. 10A). 100 μM YC-1 had the same effect (FIG. 10A). When the cells were simultaneously treated with YC-1 and 100 μM SNP, the cGMP levels doubled compared to the cGMP levels after stimulation with SNP alone (FIG. 10A). Similar results were obtained with rhsGC in cell extracts.

ODQ is described as a selective inhibitor of NO-stimulated sGC that, however, does not inhibit the basal activity (Garthwaite et al., 1995). In Sf9 cells expressing rhsGC (after expression with the recombinant baculoviruses described above, without GST-tag), ODQ did not have an influence on the basal cGMP levels; the stimulation of rhsGC in. intact cells with SNP, however, was inhibited by simultaneous incubation with ODQ (FIG. 10B).

EXAMPLE 7

Extraction of the Purified Human Soluble Guanylyl Cyclase α1/β1 (hsGCα1/β1)

For the purification of recombinant human hsGCα1/β1 from Sf9 cells, a recombinant baculovirus [see Example 2] was used in which a fusion protein composed of hsGCα1 and attached GST [so-called GST-tag, GST=glutathione-S-transferase from *Schistosoma japonicum*; see Example 2] is formed. Using this GST-tag, which binds to glutathione with high affinity, specific affinity chromatography on glutathione sepharose 4B (Pharmacia, Freiburg, Germany) can be performed. The Sf9 cells coinfected with hsGCα1 baculoviruses (with GST-tag) and hsGCβ1 baculoviruses (without GST-tag) were lysed in 25 mM triethanolamine pH 7.8/1 mM EDTA/5 mM DTT/1 μM leupeptin/0.5 μg/ml trypsin inhibitor/0.2 mM PMSF (30 min hypotonic lysis at 4° C.). After addition of NaCl (75 mM final concentration), the homogenate was centrifuged at 75,000×g for 1 hour at 4° C. The supernatant was mixed with the GSH sepharose 4B for 1 hour at room temperature. The glutathione sepharose 4B was then pelleted by centrifugation at 500×g for 5 minutes and the supernatant removed. A 10-fold volume of 50 mM Tris-HCl (pH 8.0)/150 mM NaCl/2.5 mM CaCl$_2$/0.1% 2-mercaptoethanol was added to the glutathione sepharose 4B and mixed for 1 minute. The mixture was centrifuged again at 500×g for 5 minutes. The supernatant was removed and the glutathione sepharose 4B was washed again in the same way. To elute from the sepharose, the hsGCα1 protein (with the bound hsGCβ1) was cleaved by thrombin from the GST-tag, which remained bound to the glutathione sepharose 4B at the specific cleavage site. Digestion with thrombin was performed in 50 mM Tris-HCl (pH 8.0)/150 mM NaCl/2.5 mM CaCl$_2$/0.1% 2-mercaptoethanol with 0.25 to 1 units thrombin/ml buffer for 1 or 3 hours at room temperature. The glutathione sepharose 4B (with the GST-tag) was pelleted again by centrifugation at 500×g for 5 minutes and the supernatant containing the hsGCα1/β1 was removed. Another elution method was performed by addition of 50 mM Tris-HCl (pH 8.0)/5 mM reduced glutathione and mixing for 30 minutes at room temperature. In this manner, hsGCα1/β1 with the GST-tag bound was removed from the glutathione sepharose 4B. After centrifugation at 500×g for 5 minutes, the supernatant containing dissolved GST-hsGCα1/β1 was removed.

By the elution with thrombin, a two-fold selectivity is achieved in a single affinity chromatographic step:

1.) Only proteins that have an affinity to reduced glutathione are able to bind.

2.) Of these proteins, only the proteins that are cleaved by thrombin will elute (as cleavage products).

The thrombin can be separated from the sample with a p-aminobenzamidine column to which thrombin binds specifically.

Figure 12:
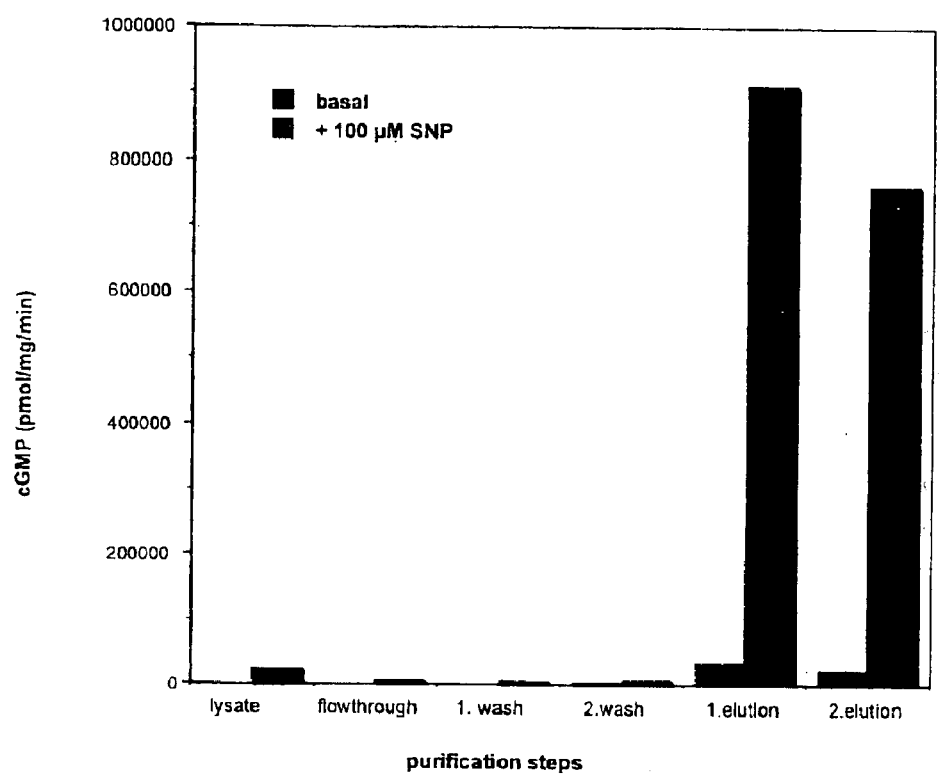

FIG. 12 shows the specific enrichment of sGC activity after elution from the GSH sepharose 4B with glutathione compared with the activity in the lysate of infected Sf9 cells.

Figure 14:
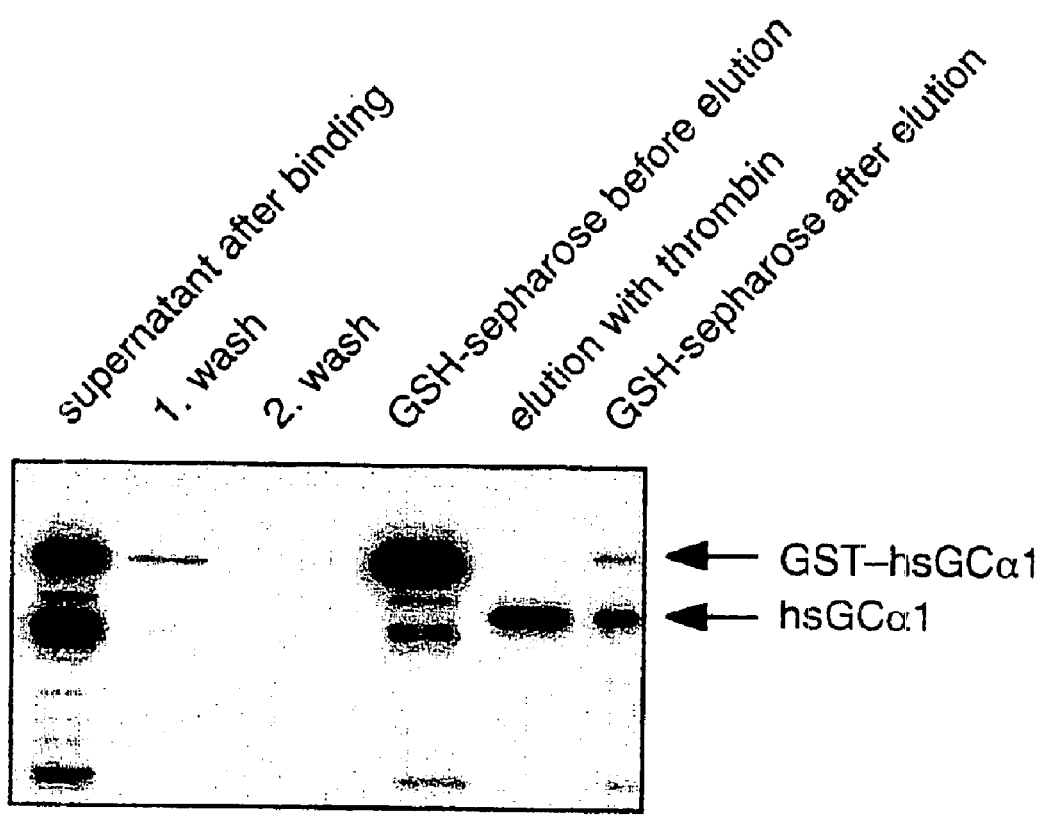

FIG. 14 shows the binding of GST-hsGCα1 to glutathione sepharose 4B and the cleavage of hsGCα1 from the GST-tag by thrombin in an immunoblot.

Figure 15:
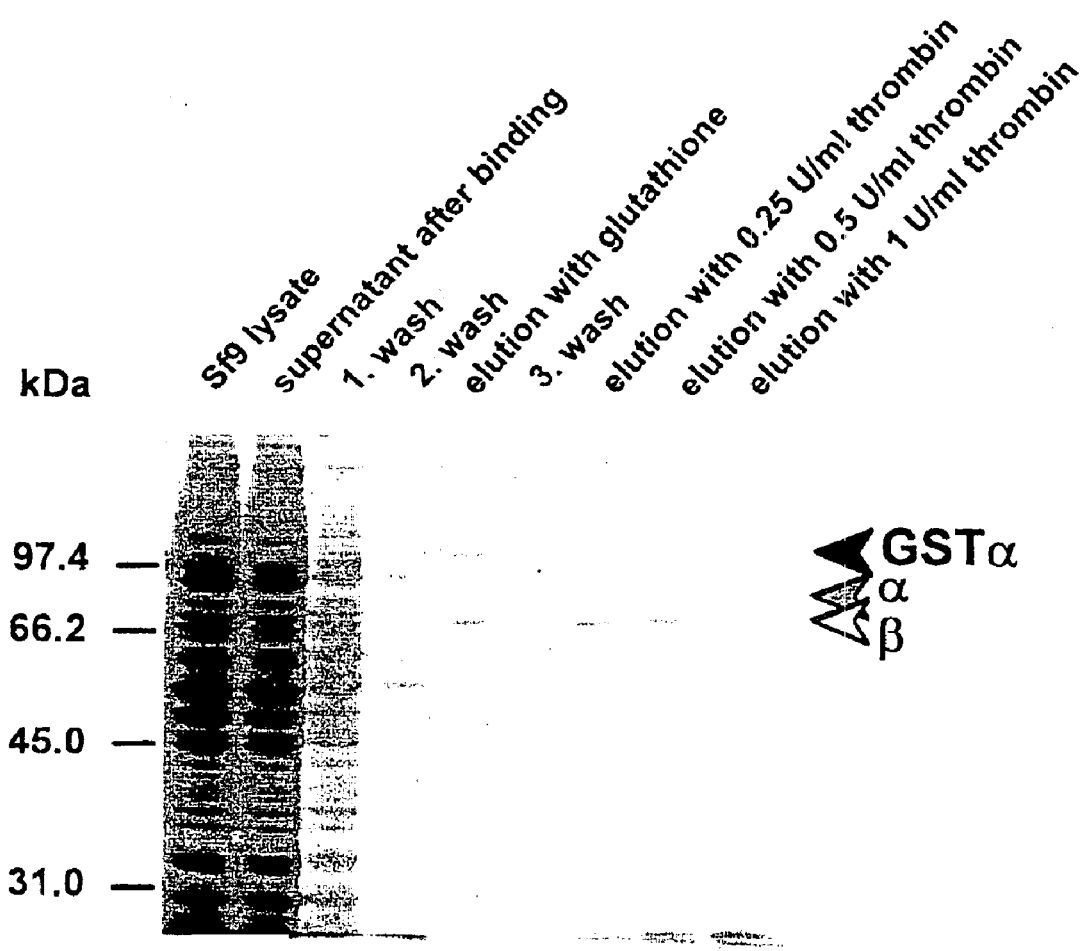

FIG. 15 shows the purification of coexpressed hsGCα1 with GST-tag and hsGCβ1 without GST-tag by affinity chromatography on glutathione sepharose 4B in a Coomassie Brilliant Blue R250-stained SDS-polyacrylamide gel. Upon elution with reduced glutathione, only two bands were visible, which correspond to GST-hsGCα1 (larger product) and hsGCβ1 (smaller product) (detected in an immunoblot). After elution with thrombin (0.25, 0.5, or 1 unit/ml for three hours at room temperature), however, the lower band was identical (hsGCβ1; estimated molecular weight according to the migration in the gel of approximately 70 kDa), whereas the upper band was significantly smaller compared to elution with glutathione (hsGCα1; estimated molecular weight of approximately 80 kDa) because the GST-tag was cleaved off by use of the thrombin elution. This approximately corresponds to the molecular weights of 77.5 kDa for hsGCα1 and 70.5 kDa for hsGCβ1 deduced from the amino acid sequences. In contrast to the elution with reduced glutathione, an additional very small band of approximately 25 kDa was visible after the thrombin elution, which is likely thrombin itself. Thrombin can be removed from the eluate by means of an aminobenzamidine sepharose column to which thrombin binds specifically. Additional bands were not detectable in this experiment.

EXAMPLE 8

Production of Polyclonal Rabbit Antisera to hsGCα1 and hsGCβ1

Antisera were obtained by immunization of rabbits with synthetic peptides corresponding to sequences from hsGCα1 (Phe-Thr-Pro-Arg-Ser-Arg-Glu-Glu-Leu-Pro-Pro-Asn-Phe-Pro [FIG. 22/SEQ ID NO: 5]; amino acids 634–647) and from hsGCβ1 (Lys-Gly-Lys-Lys-Glu-Pro-Met-Gln-Val-Trp-Phe-Leu-Ser-Arg-Lys-Asn-Thr-Gly-Thr-Glu-Glu-Thr [FIG. 23/SEQ ID NO: 6] amino acids 593–614) that were coupled to KLH (keyhole limpet hemocyanin) via an additional C-terminal (α1) or N-terminal (β1) cysteine residue. The antisera were affinity-purified with the corresponding peptides coupled to epoxy-activated sepharose (Pharmacia, Freiburg, Germany) according to the manufacturer's instructions.

EXAMPLE 9

Detection of hsGCα1 and hsGCβ1 in Different Human Tissues by Immunoblotting

Human lung tissue was obtained from a tumor-free area of a lung resection, and human cortex and cerebellum were from a normal autopsy. All tissues were immediately frozen in liquid nitrogen and stored at −70° C. The frozen tissues were homogenized in a mortar and double-concentrated, hot SDS stop buffer (130 mM Tris-HCl, pH 6.8/16% [v/v] glycerol/4% [w/v] SDS/0.025% [w/v] bromphenol blue/6.5% [v/v] 2-mercaptoethanol) was added to the powder. This was incubated at 95° C. for 10 minutes and then centrifuged at 20,000×g for 20 minutes. The supernatant was used for immunoblotting (for antibodies used, see above).

Figure 13:
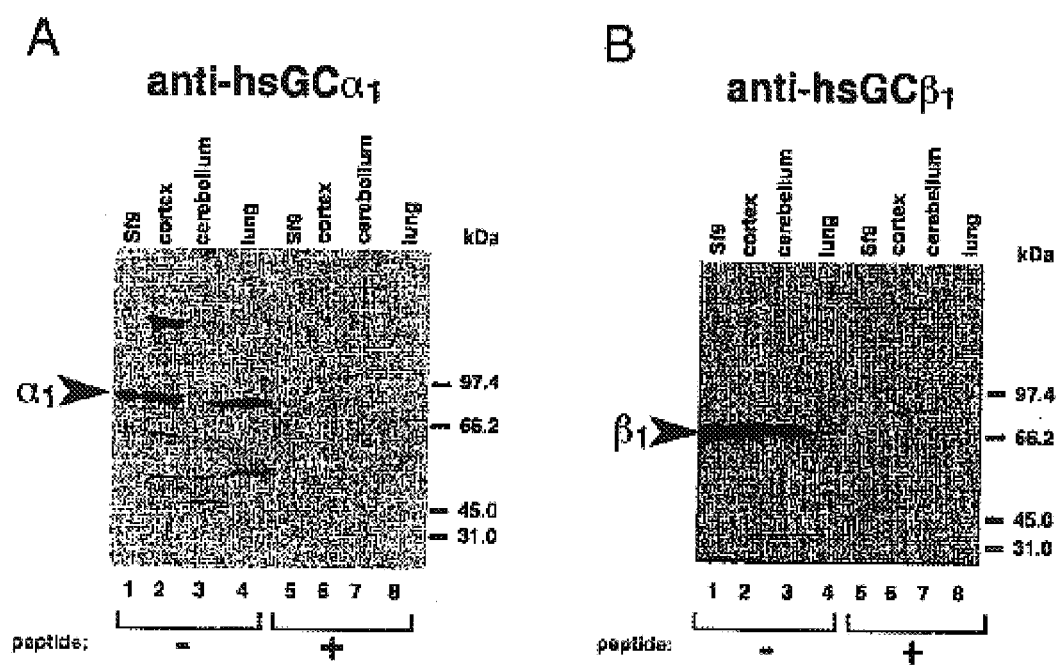

Expression of both subunits (α1 and β1) was detected in all three tissues (FIG. 13). In contrast, expression could not be detected in kidney, liver, and pancreas (data not shown).

EXAMPLE 10

Construction of Recombinant Adenoviral hsGC Vectors

Figure 16:
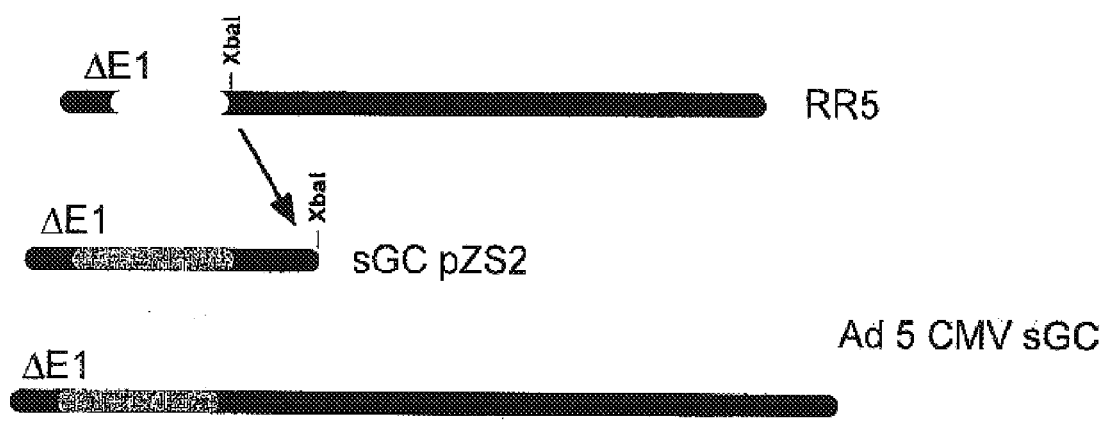

The cDNAs for hsGCα1 and hsGCβ1 were isolated from the original plasmid with the restriction enzyme EcoRI as 3.0 kb (hsGCα1) and 2.4 kb (hsGCβ3) fragments. The fragments were each inserted into the EcoRI restriction sites of the adenoviral transfer plasmid pZS2 (FIG. 16), which contains an adenovirus type 5 sequence (Ad5) with a deletion in the E1 region (ΔE1), followed by an expression cassette with a CMV (cytomegalovirus) promotor/enhancer and a unique XbaI restriction site. hsGCα1-pZS2 and hsGCβ1-pZS2 digested with XbaI were inserted into the XbaI site of the long arm (RR5) of Ad5 (FIG. 16). The resulting recombinant adenoviral vectors Ad5CMVhsGCα1 and Ad5CMVhsGCβ1 are replication deficient because they lack the E1 region. To propagate the viruses, 293 cells that express E1 were infected with these viruses. Viral plaques appeared 12–24 hours after the transfection. Viruses from single plaques were purified according to a standard procedure. Plaques containing recombinant viruses (Ad5CMVhsGCα1 or Ad5CMVhsGCβ1) were identified by means of PCR analysis: The plaque material was freeze-thawed three times, incubated at 37° C. for 30 minutes in lysis buffer (16.6 mM ammonium sulfate/6.7 mM Tris-HCl pH 6.8/6.7 mM MgCl$_2$/5 mM 2-mercaptoethanol/6.7 mM EDTA/1.7 mM SDS/50 µg/ml proteinase K), and thereafter heat inactivated for 10 minutes at 85° C. Finally, the DNA was isolated from the lysate with a standard phenol/chloroform extraction and used for PCR analysis.

EXAMPLE 11

Detection of cGMP Formation in EA.hy926 Cells after Coinfection with the hsGC Adenovectors Ad5CMVhsGCα1 and Ad5CMVhsGCβ1

Figure 17:
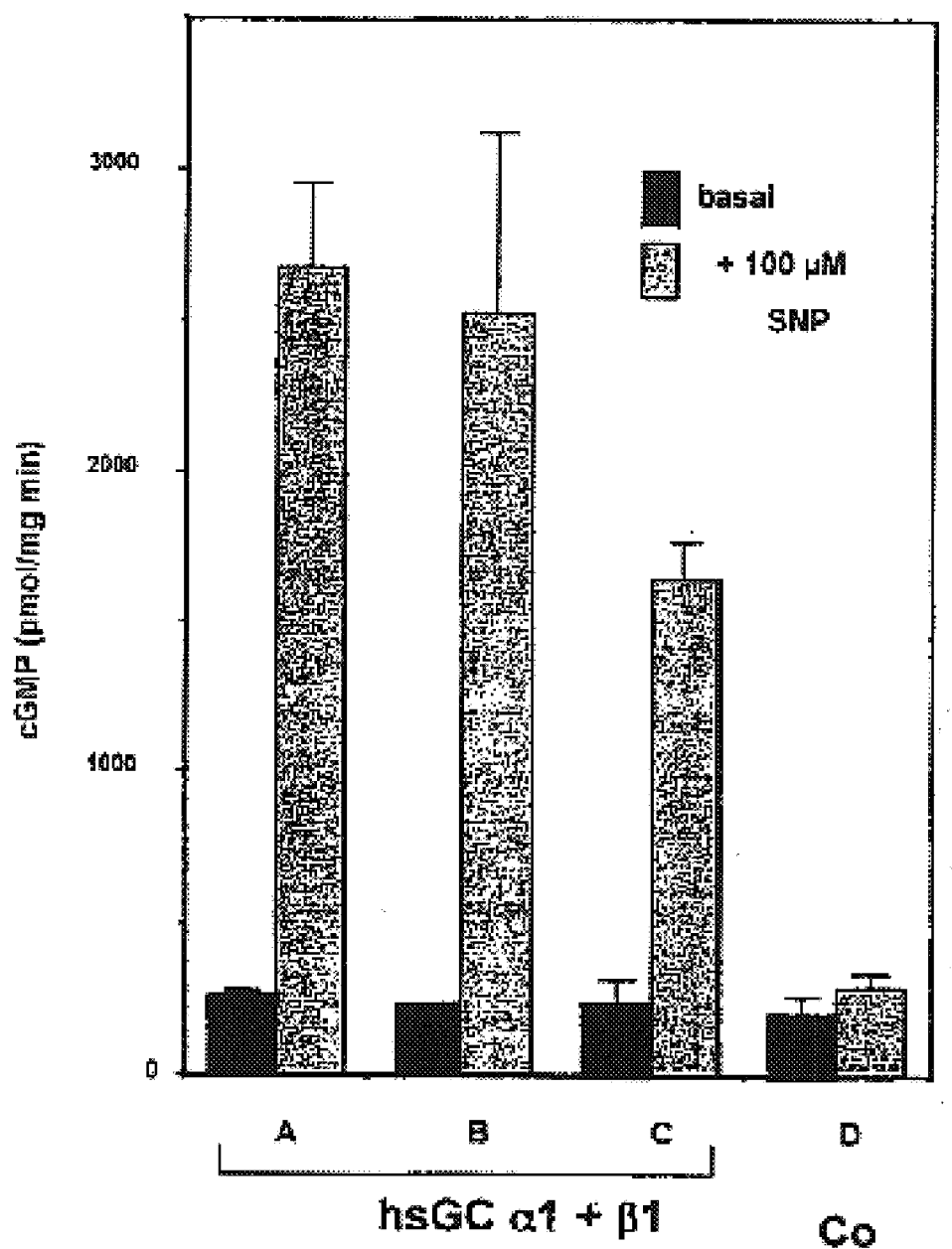

Ten 10-cm cell culture dishes with 'EA.hy926' cells were coinfected with each of the adenovectors Ad5CMVhsGCα1 and Ad5CMVhsGCβ1 at 2×10$^{10}$ pfu (plaque forming units) per dish. After 72 hours, the cells were harvested by adding hypotonic lysis buffer (25 mM triethanolamine pH 7.8/1 mM EDTA/5 mM DTT/1 µM leupeptin/0.5 mg/l trypsin inhibitor/0.2 mM PMSF) and detaching with a cell scraper. The homogenate was centrifuged at 500×g for 15 minutes and the supernatant was mixed with an equal volume of glycerol and stored at −20° C. The stimulation of hsGC by 100 µM SNP (sodium nitroprusside) was determined by measurement of the basal cGMP level and the cGMP level after treatment with SNP according to the procedure described above (see Example 5). In three samples (A, B, C), a 7-fold to 10.75-fold elevation in the cGMP concentration compared to the basal activity was detectable after SNP stimulation, while no significant elevation was measurable in the control without adenovirus infection (FIG. 17).

REFERENCES

Bradford, M. M. (1976) *Annal. Biochem.* 72: 248–254.

Friebe, A.; Schultz, G.; Koesling, D. (1996) *EMBO J.* 15: 6863–6868.

Garthwaite, J.; Southam, E.; Boulton, C. L.; Nielsen, E. B.; Schmidt, K.; Mayer, B. (1995) *Mol. Pharmacol.* 48: 184–188.

Giuili, G.; Scholl, U.; Bulle, F.; Guellaen, G. (1992) *FEBS Lett.* 304: 83–88.

Guthmann, F.; Mayer, B.; Koesling, D.; Kukovetz, W. R.; Böhme, E. (1992) *Naunyn-Schmiedeberg's Arch. Pharmacol.* 346: 537–541.

Harteneck, C.; Wedel, B.; Koesling, D.; Malkewitz, J.; Böhme, E.; Schultz, G. (1991) *FEBS Lett.* 292: 217–222.

Humbert, P.; Niroomand, F.; Fischer, G.; Mayer, B.; Koesling, D.; Hinsch, K.-D.; Gausepohl, H.; Frank, R.; Schultz, G.; Böhme, E. (1990) *Eur. J. Biochem.* 190: 273–278.

Ko, F. N.; Wu, C. C.; Kuo, S.-C.; Lee, F.-Y.; Teng, C. M. (1994) *Blood* 84: 4226–4233.

Koesling, D.; Herz, J.; Gausepohl, H.; Niroomand, F.; Hinsch, K.-D.; Mülsch, A.; Böhme, E.; Schultz, G.; Frank, R. (1988) *FEBS Lett.* 239: 29–34.

Schmidt, H. H. H. W.; Walter, U. (1994) *Cell* 78: 919–925.

Schultz, G.; Böhme, E. (1984) published in: Bergmeyer, H. U.; Bergmeyer, J.; Graβl, M. (Eds.): Methods of Enzymatic Analysis, Vol. 4, Verlag Chemie, Weinheim, pages 379–389.

Wu, C.-C.; Ko, F.-N.; Kuo, S.-C.; Lee, F.-Y.; Teng, C.-M. (1995) *British J. Pharmacol.* 116:1973–1978.

What is claimed is:

1. Isolated soluble guanylyl cyclase α 1/β1, which is an enzymatically active heterodimer comprising hsGCα1 polypeptide SEQ ID NO: 2 and hsGCβ1 polypeptide SEQ ID NO: 4.

2. A method for the production of hsGCα1 polypeptide SEQ ID NO:2 and hsGC β1 polypeptide SEQ ID NO:4 subunits of soluble guanylyl cyclase comprising the expression in prokaryotic or eukaryotic host cells of expression vectors comprising the polynucleotide sequence encoding said of hsGCα1 polypeptide SEQ ID NO:2 and hsGCβ1 polypeptide SEQ ID NO:4 and obtaining the subunits.

3. The method for producing the α 1 and β1 subunits of soluble guanylyl cyclase according to claim 2, wherein the step of obtaining the subunits comprises a lysis of the cells, the affinity chromatography of the cell lysate, and the subsequent elution of the subunits.

4. The method for producing the α 1 and β1 subunits of soluble guanylyl cyclase according to claim 2 or 3, wherein the expression vector comprises at least one additional polynucleotide sequence coding for a domain for the specific affinity chromatography (affinity tag) with appended protease cleavage site.

5. The method for producing α1 and β1 subunits of soluble guanylyl cyclase according to claim 4, wherein the expression vector comprises the polynucleotide sequence encoding hsGCα1 polypeptide SEQ ID NO:2 with affinity tag, or the polynucleotide sequence encoding hsGCβ1 polypeptide SEQ ID NO:4 with affinity tag, or the polynucleotide sequence encoding hsGCα1 polypeptide SEQ ID NO:2 with affinity tag, and the polynucleotide sequence encoding hsGCβ1 polypeptide SEQ ID NO:4, or the polynucleotide sequence encoding hsGCβ1 polypeptide SEQ ID NO:4 with affinity tag and the polynucleotide sequence encoding hsGCα1 polypeptide SEQ ID NO:2, or the polynucleotide sequence encoding hsGCα1 polypeptide SEQ ID NO:2 with affinity tag and the polynucleotide sequence encoding hsGCα1 polypeptide SEQ ID NO:4 with affinity tag.

6. The method for producing soluble guanylyl cyclase α 1/β1, which is an enzymatically active heterodimer comprising hsGCα1 polypeptide SEQ ID NO:2 and hsGCβ1 polypeptide SEQ ID NO:4, the method comprising the separate expression in prokaryotic or eukaryotic host cells of an expression vector comprising the polynucleotide sequence encoding said hsGCα1 polypeptide SEQ ID NO:2 or hsGCβ1 polypeptide SEQ ID NO:4, extraction of the subunits, and reconstitution of said subunits polypeptide SEQ ID NO:2 and hsGCβ1 polypeptide SEQ ID NO:4 to form the dimeric guanylyl cyclase α 1/β1.

7. The method for producing soluble guanylyl cyclase α 1/β1 according to claim 6, wherein the step for the purification of the subunits consists of a separate lysis of cells comprising hsGCα1 polypeptide SEQ ID NO:2 or hsGCβ1 polypeptide SEQ ID NO:4, the separate affinity chromatography of the cell lysates, and the subsequent elution of the subunits.

8. The method for producing soluble guanylyl cyclase α 1/β1, which is an enzymatically active heterodimer comprising hsGCα1 polypeptide SEQ ID NO:2 and hsGCβ1 polypeptide SEQ ID NO:4, the method consisting of the coexpression of the polynucleotide sequences encoding said hsGCα1 polypeptide SEQ ID NO:2 and hsGCβ1 polypeptide SEQ ID NO:4 in prokaryotic or eukaryotic host cells, a followed by lysis of the said host cells comprising hsGCα1 polypeptide SEQ ID NO:2 and hsGCβ1 polypeptide SEQ ID NO:4, affinity chromatography and subsequent elution of hsGCa1/p1 soluble guanylyl cyclases α 1/β1.

* * * * *